United States Patent
Hirschberg et al.

(12)

(10) Patent No.: US 6,252,141 B1
(45) Date of Patent: Jun. 26, 2001

(54) TOMATO GENE B POLYNUCLEOTIDES CODING FOR LYCOPENE CYCLASE

(75) Inventors: Joseph Hirschberg, Jerusalem; Gil Ronen, Beer-Sheva; Dany Zamir, Gedera, all of (IL)

(73) Assignee: Yissum Research and Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/134,607

(22) Filed: Aug. 14, 1998

(51) Int. Cl.[7] ............................. A01H 5/00; C12N 1/21; C12N 5/14; C12N 15/82
(52) U.S. Cl. ................... 800/298; 435/252.3; 435/419; 536/23.2
(58) Field of Search ................... 536/23.2, 23.6, 536/24.5; 435/419, 468, 252.3; 800/298, 286

(56) References Cited

U.S. PATENT DOCUMENTS 5,585,479 * 12/1996 Hoke et al. .................... 536/24.5
5,792,903 * 8/1998 Hirschberg et al. .............. 800/200

FOREIGN PATENT DOCUMENTS

WO 96/36717 * 11/1996 (WO).

OTHER PUBLICATIONS

Stam M, et al. "The silence of genes in transgenic plants." Ann. Bot. 79: 3–12, 1997.*

Koziel MG, et al. "Optimizing expression of transgenes with an emphasis on post–transcriptional events." Plant Mol. Biol. 32: 393–405, 1996.*

Smith CJS, et al. "Antisense RNA inhibition of polygalacturonase gene expression in transgenic tomatoes." Nature 334: 724–726, Aug. 25, 1988.*

* cited by examiner

Primary Examiner—Amy J. Nelson

(57) ABSTRACT

An isolated complementary and genomic DNA segment encoding lycopene cyclase of the B locus of tomato are provided.

5 Claims, 4 Drawing Sheets

SEQUENCE LISTING (1) GENERAL INFORMATION:

(iii) NUMBER OF SEQUENCES:    25

(2) INFORMATION FOR SEQ ID NO:1:

(i) SEQUENCE CHARACTERISTICS:
        (A) LENGTH:22
        (B) TYPE:nucleic acid
        (C) STRANDEDNESS:single
        (D) TOPOLOGY:linear (xi) SEQUENCE DESCRIPTION:SEQ ID NO:1:

AATGGAAGCT CTTCTCAAGC CT    22

(2) INFORMATION FOR SEQ ID NO:2:

(i) SEQUENCE CHARACTERISTICS:
        (A) LENGTH:23
        (B) TYPE:nucleic acid
        (C) STRANDEDNESS:single
        (D) TOPOLOGY:linear (xi) SEQUENCE DESCRIPTION:SEQ ID NO:2:

CACATTCAAA GGCTCTCTAT CGC                                         23

(2) INFORMATION FOR SEQ ID NO:3:

(i) SEQUENCE CHARACTERISTICS:
        (A) LENGTH:16
        (B) TYPE:nucleic acid
        (C) STRANDEDNESS:single
        (D) TOPOLOGY:linear (xi) SEQUENCE DESCRIPTION:SEQ ID NO:3:

TCGAGAACGG ACGATG                                                    16

(2) INFORMATION FOR SEQ ID NO:4:

(i) SEQUENCE CHARACTERISTICS:
        (A) LENGTH:16
        (B) TYPE:nucleic acid
        (C) STRANDEDNESS:single
        (D) TOPOLOGY:linear (xi) SEQUENCE DESCRIPTION:SEQ ID NO:4:

TGCAGAGAGA CAGATG                                                    16

(2) INFORMATION FOR SEQ ID NO:5:

(i) SEQUENCE CHARACTERISTICS:
        (A) LENGTH:22
        (B) TYPE:nucleic acid
        (C) STRANDEDNESS:single
        (D) TOPOLOGY:linear (xi) SEQUENCE DESCRIPTION:SEQ ID NO:5:

ATTTCATGCT TTATCTTTGA AG                                          22

(2) INFORMATION FOR SEQ ID NO:6:

(i) SEQUENCE CHARACTERISTICS:
        (A) LENGTH:20
        (B) TYPE:nucleic acid
        (C) STRANDEDNESS:single
        (D) TOPOLOGY:linear (xi) SEQUENCE DESCRIPTION:SEQ ID NO:6:

GCTGAAGTTG AAATTGTTGA                                             20

(2) INFORMATION FOR SEQ ID NO:7:

(i) SEQUENCE CHARACTERISTICS:
        (A) LENGTH:20
        (B) TYPE:nucleic acid
        (C) STRANDEDNESS:single
        (D) TOPOLOGY:linear (xi) SEQUENCE DESCRIPTION:SEQ ID NO:7:

TCTCTTCCTC AATAACACTT                                             20

(2) INFORMATION FOR SEQ ID NO:8:

(i) SEQUENCE CHARACTERISTICS:
        (A) LENGTH:1666
        (B) TYPE:nucleic acid
        (C) STRANDEDNESS:double
        (D) TOPOLOGY:linear (xi) SEQUENCE DESCRIPTION:SEQ ID NO:8:

```
ATGGAAGCTC TTCTCAAGCC TTTTCCATCT CTTTTACTTT CCTCTCCTAC         50

ACCCCATAGG TCTATTTTCC AACAAAATCC CTCTTTTCTA AGTCCCACCA        100

CCAAAAAAAA ATCAAGAAAA TGTCTTCTTA GAAACAAAAG TAGTAAACTT        150

TTTTGTAGCT TTCTTGATTT AGCACCCACA TCAAAGCCAG AGTCTTTAGA        200

TGTTAACATC TCATGGGTTG ATCCTAATTC GAATCGGGCT CAATTCGACG        250

TGATCATTAT CGGAGCTGGC CCTGCTGGGC TCAGGCTAGC TGAACAAGTT        300

TCTAAATATG GTATTAAGGT ATGTTGTGTT GACCCTTCAC CACTCTCCAT        350

GTGGCCAAAT AATTATGGTG TTTGGGTTGA TGAGTTTGAG AATTTAGGAC        400

TGGAAAATTG TTTAGATCAT AAATGGCCTA TGACTTGTGT GCATATAAAT        450

GATAACAAAA CTAAGTATTT GGGAAGACCA TATGGTAGAG TTAGTAGAAA        500

GAAGCTGAAG TTGAAATTGT TGAATAGTTG TGTTGAGAAC AGAGTGAAGT        550

TTTATAAAGC TAAGGTTTGG AAAGTGGAAC ATGAAGAATT TGAGTCTTCA        600

ATTGTTTGTG ATGATGGTAA AAGATAAGA GGTAGTTTGG TTGTGGATGC         650

AAGTGGTTTT GCTAGTGATT TTATAGAGTA TGACAGGCCA AGAAACCATG        700

GTTATCAAAT TGCTCATGGG GTTTTAGTAG AAGTTGATAA TCATCCATTT        750

GATTTGGATA AAATGGTGCT TATGGATTGG AGGGATTCTC ATTTGGGTAA        800

TGAGCCATAT TTAAGGGTGA ATAATGCTAA AGAACCAACA TTCTTGTATG        850

CAATGCCATT TGATAGAGAT TTGGTTTTCT TGGAAGAGAC TTCTTTGGTG        900

AGTCGTCCTG TTTTATCGTA TATGGAAGTA AAAAGAAGGA TGGTGGCAAG        950

ATTAAGGCAT TTGGGGATCA AAGTGAAAAG TGTTATTGAG GAAGAGAAAT       1000

GTGTGATCCC TATGGGAGGA CCACTTCCGC GGATTCCTCA AAATGTTATG       1050

GCTATTGGTG GGAATTCAGG GATAGTTCAT CCATCAACAG GGTACATGGT       1100

GGCTAGGAGC ATGGCTTTAG CACCAGTACT AGCTGAAGCC ATCGTCGAGG       1150

GGCTTGGCTC AACAAGAATG ATAAGAGGGT CTCAACTTTA CCATAGAGTT       1200

TGGAATGGTT TGTGGCCTTT GGATAGAAGA TGTGTTAGAG AATGTTATTC       1250

ATTTGGGATG GAGACATTGT TGAAGCTTGA TTTGAAAGGG ACTAGGAGAT       1300

TGTTTGACGC TTTCTTTGAT CTTGATCCTA AATACTGGCA AGGGTTCCTT       1350

TCTTCAAGAT TGTCTGTCAA AGAACTTGGT TTACTCAGCT TGTGTCTTTT       1400

CGGACATGGC TCAAACATGA CTAGGTTGGA TATTGTTACA AAATGTCCTC       1450

TTCCTTTGGT TAGACTGATT GGCAATCTAG CAATAGAGAG CCTTTGAATG       1500

TGAAAAGTTT GAATCATTTT CTTCATTTTA ATTTCTTTGA TTATTTTCAT       1550

ATTTTCTCAA TTGCAAAAGT GAGATAAGAG CTACATACTG TCAACAAATA       1600

AACTACTATT GGAAAGTTAA AATATGTGTT TGTTGTATGT TATTCTAATG       1650

GAATGGATTT TGTAAA                                            1666
```

(2) INFORMATION FOR SEQ ID NO:9:

(i) SEQUENCE CHARACTERISTICS:
        (A) LENGTH:2876
        (B) TYPE:nucleic acid
        (C) STRANDEDNESS:double
        (D) TOPOLOGY:linear (xi) SEQUENCE DESCRIPTION:SEQ ID NO:9:

```
GAATTCTCTG AAAAGGAGCA CCATATTTGC CGCACTGTGG TTCATATTTC         50
CAAGTACATT TAGATGAACT ATATCATCAG ATTGAAAGGT TATTGTATAA        100
TCAATCCAGT GGATTCTCGT TCTGGCACCT TTAGAAGTAC ATGTGCGGAA        150
AAGAATGATA AGGTTTGTAT TGTTGTTGAC AAAGCCTGTT GCCTTTCTCA        200
TTTGTAAATG TTCTGAACGA CTCCTAAATT ACTCTTAAGG TGTAAGGTCT        250
TCCGTGCCTG TTTGTAAATA TAATGCTGTG CCGTGACTTA CCTTTTGTAC        300
CATTTGTTCA AATGTATGGC CTGAACACCA GGGTTGTCAA AAATGTCTCA        350
TGCCCGTTTT ATTGGTCTGA AAATGGCGTG ATGCCAAATT CTGCCGCTCC        400
ACAGTGAGCA TTTCGATCTA CTGGAAATTG ACCAACTTAT TTTATCACTT        450
GATAACTAAA CAAAATCCTA TTAACTTTAA TCATACATTG TATTTATACC        500
GAAAAATTTA TGCATAACTC ATTAAATTAC CTTTTTTAGC AGTCAAATTC        550
TAAATCAGTT TCTAATTTAT CAAAATGGCT TTTATAGGGT CCCATTTCCA        600
CTAATATACC TGCCGTCCAT GCACTGACTA CAAAACAAAT ACCTCACTAT        650
GTTTGTTAGT GCTTGGTAAT ATAAAACCTT TTCTTTTATG AGAAAGTTCA        700
CCGAGAATAA TTTTCTATTT GTGGCATAAT AGTATATAGT GCAGATTGAC        750
AAGAATTTAA TTTTGCAGTT GGGCACATGA ACAATTTTCC TCAAAGTTGT        800
AGAAAGTACT TTTCATTTTC TTGTCACCGA AAATTATTTA TAATTGAAAT        850
TAAAACCGAA TGAGCTGCAA GATTCAAGTC GAATTTTCAA AAGAATTGAC        900
CAAGAAAAAA TTCAAAAATA TCCCCCACCC CCTACCAAAC ACATCCTAAA        950
GTGAGGTATA GACTGGGACT GGGATTGGGA AAAGGGTAAA ATGCTTTCAC       1000
TAGCTTAGCA AAGATTCCAC TTTGTTAGCT ATCTTTCTTT CTCATTTCCT       1050
TTTTTCTTTT TCTTTTTTTT GTTATATAAG CCAAAGTAGG TACCCAAAAG       1100
CATCAATATT TTGTATTGCT TGGTGATTCC TCTGTAGTCC AGTATTTCAT       1150
TTTCTACAAG TTCCACCTCC CTCCATAATT AACCATTATC AATCTTATAC       1200
ATTCTCTATA ATGGAAACTC TTCTCAAGCC TTTTCCATCT CTTTTACTTT       1250
CCTCTCCTAC ACCCCATAGG TCTATTTTCC AACAAAATCC CTCTTTTCTA       1300
AGTCCCACCA CCAAAAAAAA ATCAAGAAAA TGTCTTCTTA GAAACAAAAG       1350
TAGTAAACTT TTTTGTAGCT TTCTTGATTT AGCACCCACA TCAAAGCCAG       1400
AGTCTTTAGA TGTTAACATC TCATGGGTTG ATCCTAATTC GAATCGGGCT       1450
CAATTCGACG TGATCATTAT CGGAGCTGGC CCTGCTGGGC TCAGGCTAGC       1500
TGAACAAGTT TCTAAATATG GTATTAAGGT ATGTTGTGTT GACCCTTCAC       1550
CACTCTCCAT GTGGCCAAAT AATTATGGTG TTTGGGTTGA TGAGTTTGAG       1600
AATTTAGGAC TGGAAAATTG TTTAGATCAT AAATGGCCTA TGACTTGTGT       1650
GCATATAAAT GATAACAAAA CTAAGTATTT GGGAAGACCA TATGGTAGAG       1700
```

-continued

| | |
|---|---|
| TTAGTAGAAA GAAGCTGAAG TTGAAATTGT TGAATAGTTG TGTTGAGAAC | 1750 |
| AGAGTGAAGT TTTATAAAGC TAAGGTTTGG AAAGTGGAAC ATGAAGAATT | 1800 |
| TGAGTCTTCA ATTGTTTGTG ATGATGGTAA GAAGATAAGA GGTAGTTTGG | 1850 |
| TTGTGGATGC AAGTGGTTTT GCTAGTGATT TTATAGAGTA TGACAGGCCA | 1900 |
| AGAAACCATG GTTATCAAAT TGCTCATGGG GTTTTAGTAG AAGTTGATAA | 1950 |
| TCATCCATTT GATTTGGATA AAATGGTGCT TATGGATTGG AGGGATTCTC | 2000 |
| ATTTGGGTAA TGAGCCATAT TTAAGGGTGA ATAATGCTAA AGAACCAACA | 2050 |
| TTCTTGTATG CAATGCCATT TGATAGAGAT TTGGTTTTCT TGGAAGAGAC | 2100 |
| TTCTTTGGTG AGTCGTCCTG TTTTATCGTA TATGGAAGTA AAAAGAAGGA | 2150 |
| TGGTGGCAAG ATTAAGGCAT TTGGGGATCA AAGTGAAAAG TGTTATTGAG | 2200 |
| GAAGAGAAAT GTGTGATCCC TATGGGAGGA CCACTTCCGC GGATTCCTCA | 2250 |
| AAATGTTATG GCTATTGGTG GGAATTCAGG GATAGTTCAT CCATCAACAG | 2300 |
| GGTACATGGT GGCTAGGAGC ATGGCTTTAG CACCAGTACT AGCTGAAGCC | 2350 |
| ATCGTCGAGG GGCTTGGCTC AACAAGAATG ATAAGAGGGT CTCAACTTTA | 2400 |
| CCATAGAGTT TGGAATGGTT TGTGGCCTTT GGATAGAAGA TGTGTTAGAG | 2450 |
| AATGTTATTC ATTTGGGATG GAGACATTGT TGAAGCTTGA TTTGAAAGGG | 2500 |
| ACTAGGAGAT TGTTTGACGC TTTCTTTGAT CTTGATCCTA AATACTGGCA | 2550 |
| AGGGTTCCTT TCTTCAAGAT TGTCTGTCAA AGAACTTGGT TTACTCAGCT | 2600 |
| TGTGTCTTTT CGGACATGGC TCAAACATGA CTAGGTTGGA TATTGTTACA | 2650 |
| AAATGTCCTC TTCCTTTGGT TAGACTGATT GGCAATCTAG CAATAGAGAG | 2700 |
| CCTTTGAATG TGAAAAGTTT GAATCATTTT CTTCATTTTA ATTTCTTTGA | 2750 |
| TTATTTTCAT ATTTTCTCAA TTGCAAAAGT GAGATAAGAG CTACATACTG | 2800 |
| TCAACAAATA AACTACTATT GGAAAGTTAA AATATGTGTT TGTTGTATGT | 2850 |
| TATTCTAATG GAATGGATTT TGTAAA | 2876 |

(2) INFORMATION FOR SEQ ID NO:10:

(i) SEQUENCE CHARACTERISTICS:
        (A) LENGTH:1740
        (B) TYPE:nucleic acid
        (C) STRANDEDNESS:double
        (D) TOPOLOGY:linear (xi) SEQUENCE DESCRIPTION:SEQ ID NO:10:

| | |
|---|---|
| ATGGAAGCTC TTCTCAAGCC TTTTCCATCT CTTTTACTTT CCTCTCCTAC | 50 |
| ACCCTATAGG TCTATTGTCC AACAAAATCC TTCTTTTCTA AGTCCCACCA | 100 |
| CCAAAAAAAA TCAAGAAAAT GTCTTCTTAG AAACAAAAGT AGTAAACTTT | 150 |
| TTGTAGCTT TCTTGATTTA GCACCCACAT CAAAGCCAGA GTCTTTAAAT | 200 |
| GTTAACATCT CATGGGTTGA TCCTAATTCG AATCGGGCTC AATTCGACGT | 250 |
| GATCATTATC GGAGCTGGCC CTGCTGGGCT CAGGCTAGCT GAACAAGTTT | 300 |
| CTAAATATGG TATTAAGGTA TGTTGTGTTG ACCCTTCACC ACTCTCCATG | 350 |
| TGGCCAAATA ATTATGGTGT TTGGGTTGAT GAGTTTGAGA ATTTAGGACT | 400 |
| GGAAAATTGT TTAGATCATA AATGGCCTAT GACTTGTGTG CATATAAATG | 450 |
| ATAACAAAAC TAAGTATTTG GGAAGACCAT ATGGTAGAGT TAGTAGAAAG | 500 |

```
AAGCTGAAGT TGAAATTGTT GAATAGTTGT GTTGAGAACA GAGTGAAGTT            550

TTATAAAGCT AAGGTTTGGA AAGTGGAACA TGAAGAATTT GAGTCTTCAA            600

TTGTTTGTGA TGATGGTAAG AAGATAAGAG GTAGTTTGGT TGTGGATGCA            650

AGTGGTTTTG CTAGTGATTT TATAGAGTAT GACAGGCCAA GAAACCATGG            700

TTATCAAATT GCTCATGGGG TTTTAGTAGA AGTTGATAAT CATCCATTTG            750

ATTTGGATAA AATGGTGCTT ATGGATTGGA GGGATTCTCA TTTGGGTAAT            800

GAGCCATATT TAAGGGTGAA TAATGCTAAA GAACCAACAT TCTTGTATGC            850

AATGCCATTT GATAGAGATT TGGTTTTCTT GGAAGAGACT TCTTTGGTGA            900

GTCGTCCTGT GTTATCGTAT ATGGAAGTAA AAAGAAGGAT GGTGGCAAGA            950

TTAAGGCATT TGGGGATCAA AGTGAAAAGT GTTATTGAGG AAGAGAAATG           1000

TGTGATCCCT ATGGGAGGAC CACTTCCGCG GATTCCTCAA AATGTTATGG           1050

CTATTGGTGG GAATTCAGGG ATAGTTCATC CATCAACAGG GTACATGGTG           1100

GCTAGGAGCA TGGCTTTAGC ACCAGTACTA GCTGAAGCCA TCGTCGAGGG           1150

GCTTGGCTCA ACAAGAATGA TAAGAGGGTC TCAACTTTAC CATAGAGTTT           1200

GGAATGGTTT GTGGCCTTTG GATAGAAGAT GTGTTAGAGA ATGTTATTCA           1250

TTTGGGATGG AGACATTGTT GAAGCTTGAT TTGAAAGGGA CTAGGAGATT           1300

GTTTGACGCT TTCTTTGATC TTGATCCTAA ATACTGGCAA GGGTTCCTTT           1350

CTTCAAGATT GTCTGTCAAA GAAACTTGGT TTACTCAGCT TGTGTCTTTT           1400

CGGACATGGC TCAAACATGA CTAGGTTGGG ATATTGTTAC AAAATGTCCT           1450

CTTCCTTTGG TTAGACTGAT TGGCAATCTA GCAATAGAGA GCCTTTGAAA           1500

TGTGAAAAGT TTGAATCATT TTCTTCATTT TAATTTCTTT GATTATTTTC           1550

ATATTTTCTC AATTGCAGAA TGAGATAAAA ACTACATACT GTCGACAAAT           1600

AAACTACTAT TGGAANGTTA AAATAATGTG TGTGTTGNAT GTTANGCCTA           1650

ATGGAANGGA TGNGGTTANG CAATTTATGA ACTGNNCGCT CTGTTCGCTT           1700

AAAANCCTTG GTTCCACCTT AANGGAANGG NCCGGCCATT                      1740

(2) INFORMATION FOR SEQ ID NO:11:

(i) SEQUENCE CHARACTERISTICS:
        (A) LENGTH:2897
        (B) TYPE:nucleic acid
        (C) STRANDEDNESS:double
        (D) TOPOLOGY:linear (xi) SEQUENCE DESCRIPTION:SEQ ID NO:11:

TGGTTCATAT TTCCAATTAC ATTTAGATGA ACTATATCAT CAGGAGTGAA             50

AGGTTATTGT ATAATCAATC CAGTGGATTC TCGTTCTGGC ACCTTTAGAA            100

GTACATGTGC GGAAAAGAAT GATAAGGTTT GTATTGTTGT TGACAAGGCC            150

TGTTGCCTTT CTCATTTGTA AATGTTCTGA ACGACTCCTA AATTACTCTT            200

AAAGTGTAAG GTCTTCCGTG CCTGTTTGTA TATATAATGC TGTGCCGTGA            250

CTTACCTTTT GTACCATTTG TTCAAATGTA TGGCCTGGAC ACTAGGGTTG            300

TCAAAAATGT CTCATGACTT CACCCTTCTT TCTTGTCTTG GTGCCCGTTT            350

TATTGGTCTG AGAACGGCGT GATGCCAAAT TCTGCCGCTC CACAGTGAGC            400

ATTTCGATCT ACTGGAAATT GACCAACTTA TTTTATCACT TGATAACTAG            450
```

```
AGTCTGGGTT CAAACAAAAT CCAATAACTT CAATCATACA TTGTATTTAT    500

ATTGAAAAAA TTATGCACAA CTCAGTAAAT TACCTTTTTT TGCAGTCAAA    550

AATTCTAGAT CAGTTTCTAA TTAATCAAAA TGGCCTTTAT AGGGTCCCAG    600

TTCCATTAAT ATACCTGCCG TCCATGCACT GATTACAAGA CAAATACCTC    650

ACTATGTTTG TTAGTGCTTG GTAATATAAA ACCTTTTCTT TTATGAGAAA    700

GTTCACCGAA ATAATTTTC TATTTGTGGC ATAACTAGTA TCGAAGTATA    750

TAGTGCAGAT TGACAAGAAT TTAATTTTGC AGTTGGGCAC ATGAACAATT    800

TTCCTCAAAG TTGTAGAAAA TATTTTTCAT TTTCTTGTCA CCGAAAATTA    850

TTTATAATTG AAATTGAAAC CGAATGAGCT GCAAGACTCG AGTCGAATTT    900

CAAAAAATT GACCAACTAA ATATGAAAAA ATCCGAATAT ATCCCCCACC    950

CCCTACCAAA CACATCCTAA AGTGAGGTAT AGACTGGGAC TGGGATTGGG    1000

AAAAGGGTAA AATGCTTTCA CTAGCTTAGC AAAGATTCCA CTTTGTTAGC    1050

TATCTTTCTT TCTCATTTCC TTTTTTCTTT TTCTTTTTTT TGTTATATAA    1100

GCCAAAGTAG GTACCCAAAA GCATCAATAT TTTGTATTGC TTGGTGATTC    1150

CTCTTTACTC CAGTATTTCA TTTTCTACAA GTTCCACCTC CCTCCATAAT    1200

TAACCATTAT CAATCTTATA CATTTTCTAT AATGGAAACT CTTCTCAAGC    1250

CTTTTCCATC TCTTTTACTT TCCTCTCCTA CACCCTATAG GTCTATTGTC    1300

CAACAAAATC CTTCTTTTCT AAGTCCCACC ACCCAAAAAA AATCAAGAAA    1350

ATGTCTTCTT AGAAACAAAA GTAGTAAACT TTTTTGTAGC TTTCTTGATT    1400

TAGCACCCAC ATCAAAGCCA GAGTCTTTAA ATGTTAACAT CTCATGGGTT    1450

GATCCTAATT CTGGTCGGGC TCAATTCGAC GTGATCATTA TCGGAGCTGG    1500

CCCTGCTGGG CTCAGGTTAG CTGAACAAGT TTCTAAATAT GGTATTAAGG    1550

TATGTTGTGT TGACCCTTCA CCACTCTCCA TGTGGCCAAA TAATTATGGT    1600

GTTTGGGTTG ATGAGTTTGA GAATTTAGGA CTGGAAGATT GTTTAGATCA    1650

TAAATGGCCT ATGACTTGTG TGCATATAAA TGATAACAAG ACTAAGTATT    1700

TGGAAGACC ATATGGTAGA GTTAGTAGAA AGAAGCTGAA GTTGAAATTG    1750

TTGAACAGTT GTGTTGAGAA CAGAGTGAAG TTTTATAAAG CTAAGGTTTG    1800

GAAAGTGGAA CATGAAGAAT TTGAGTCTTC AATTGTTTGT GATGATGGTA    1850

AGAAGATAAG AGGTAGTTTG GTTGTGGATG CAAGTGGTTT TGCTAGTGAT    1900

TTTATAGAGT ATGACAAGCC AAGAAACCAT GGTTATCAAA TTGCTCATGG    1950

GGTTTTAGTA GAAGTTGATA ATCATCCATT TGATTTGGAT AAAATGGTGC    2000

TTATGGATTG GAGGGATTCT CATTTAGGTA ATGAGCCATA TTTAAGGGTG    2050

AATAATGCTA AGAACCAAC ATTCTTGTAT GCAATGCCAT TTGATAGAAA    2100

TTTGGTTTTC TTGGAAGAGA CTTCTTTGGT GAGTCGTCCT GTGTTATCGT    2150

ATATGGAAGT AAAAAGAAGG ATGGTGGCAA GATTAAGGCA TTTGGGGATC    2200

AAAGTGAGAA GTGTTATTGA GGAAGAGAAA TGTGTGATCC CTATGGGAGG    2250

ACCACTTCCG CGGATTCCTC AAAATGTTAT GGCTATTGGT GGGAATTCAG    2300

GGATAGTTCA TCCATCAACG GGGTACATGG TGGCTAGGAG CATGGCTTTA    2350

GCACCAGTAC TAGCTGAAGC CATCGTCGAG GGGCTTGGCT CAACAAGAAT    2400

GATAAGAGGG TCTCAACTTT ACCATAGAGT TTGGAATGGT TTGTGGCCTT    2450
```

| | |
|---|---:|
| TGGATAGAAG ATGTGTTAGA GAATGTTATT CATTTGGGAT GGAGACATTG | 2500 |
| TTGAAGCTTG ATTTGAAAGG GACTAGGAGA TTGTTTGACG CTTTCTTTGA | 2550 |
| TCTTGATCCT AAATACTGGC AAGGGTTCCT TTCTTCAAGA TTGTCTGTCA | 2600 |
| AAGAACTTGG TTTACTCAGC TTGTGTCTTT TCGGACATGG CTCAAATTTG | 2650 |
| ACTAGGTTGG ATATTGTTAC AAAATGTCCT GTTCCTTTGG TTAGACTGAT | 2700 |
| TGGCAATCTA GCAGTAGAGA GCCTTTGAAT GTGAAAAGTT TGAATCATTT | 2750 |
| TCTTTATTTT AATTTCTTTG ATTATTTTCA TATTTTCTCA ATGCAAAAGT | 2800 |
| GAGAGAAGAC TATACACTGT CAACAAATAA ACTACTATTG GAAAGTTAAA | 2850 |
| ATAATGTGTG TGTTGTATGT TATGCTAATG GAATGGATTG GTGTAAA | 2897 |

(2) INFORMATION FOR SEQ ID NO:12:

(i) SEQUENCE CHARACTERISTICS:
        (A) LENGTH:1740
        (B) TYPE:nucleic acid
        (C) STRANDEDNESS:double
        (D) TOPOLOGY:linear (xi) SEQUENCE DESCRIPTION:SEQ ID NO:12:

| | |
|---|---:|
| ATGGAAGCTC TTCTCAAGCC TTTTCCATCT CTTTTACTTT CCTCTCCTAC | 50 |
| ACCCTATAGG TCTATTGTCC AACAAAATCC TTCTTTTCTA AGTCCCACCA | 100 |
| CCAAAAAAAA TCAAGAAAAT GTCTTCTTAG AAACAAAAGT AGTAAACTTT | 150 |
| TTTGTAGCTT TCTTGATTTA GCACCCACAT CAAAGCCAGA GTCTTTAAAT | 200 |
| GTTAACATCT CATGGGTTGA TCCTAATTCG AATCGGGCTC AATTCGACGT | 250 |
| GATCATTATC GGAGCTGGCC CTGCTGGGCT CAGGCTAGCT GAACAAGTTT | 300 |
| CTAAATATGG TATTAAGGTA TGTTGTGTTG ACCCTTCACC ACTCTCCATG | 350 |
| TGGCCAAATA ATTATGGTGT TTGGGTTGAT GAGTTTGAGA ATTTAGGACT | 400 |
| GGAAAATTGT TTAGATCATA AATGGCCTAT GACTTGTGTG CATATAAATG | 450 |
| ATAACAAAAC TAAGTATTTG GAAGACCAT ATGGTAGAGT TAGTAGAAAG | 500 |
| AAGCTGAAGT TGAAATTGTT GAATAGTTGT GTTGAGAACA GAGTGAAGTT | 550 |
| TTATAAAGCT AAGGTTTGGA AAGTGGAACA TGAAGAATTT GAGTCTTCAA | 600 |
| TTGTTTGTGA TGATGGTAAG AAGATAAGAG GTAGTTTGGT TGTGGATGCA | 650 |
| AGTGGTTTTG CTAGTGATTT TATAGAGTAT GACAGGCCAA GAAACCATGG | 700 |
| TTATCAAATT GCTCATGGGG TTTTAGTAGA AGTTGATAAT CATCCATTTG | 750 |
| ATTTGGATAA AATGGTGCTT ATGGATTGGA GGGATTCTCA TTTGGGTAAT | 800 |
| GAGCCATATT TAAGGGTGAA TAATGCTAAA GAACCAACAT TCTTGTATGC | 850 |
| AATGCCATTT GATAGAGATT TGGTTTTCTT GGAAGAGACT TCTTTGGTGA | 900 |
| GTCGTCCTGT GTTATCGTAT ATGGAAGTAA AAGAAGGAT GGTGGCAAGA | 950 |
| TTAAGGCATT TGGGGATCAA AGTGAAAAGT GTTATTGAGG AAGAGAAATG | 1000 |
| TGTGATCCCT ATGGGAGGAC CACTTCCGCG GATTCCTCAA AATGTTATGG | 1050 |
| CTATTGGTGG GAATTCAGGG ATAGTTCATC CATCAACAGG GTACATGGTG | 1100 |
| GCTAGGAGCA TGGCTTTAGC ACCAGTACTA GCTGAAGCCA TCGTCGAGGG | 1150 |
| GCTTGGCTCA ACAAGAATGA TAAGAGGGTC TCAACTTTAC CATAGAGTTT | 1200 |
| GGAATGGTTT GTGGCCTTTG GATAGAAGAT GTGTTAGAGA ATGTTATTCA | 1250 |

| | |
|---|---:|
| TTTGGGATGG AGACATTGTT GAAGCTTGAT TTGAAAGGGA CTAGGAGATT | 1300 |
| GTTTGACGCT TTCTTTGATC TTGATCCTAA ATACTGGCAA GGGTTCCTTT | 1350 |
| CTTCAAGATT GTCTGTCAAA GAAACTTGGT TTACTCAGCT TGTGTCTTTT | 1400 |
| CGGACATGGC TCAAACATGA CTAGGTTGGG ATATTGTTAC AAAATGTCCT | 1450 |
| CTTCCTTTGG TTAGACTGAT TGGCAATCTA GCAATAGAGA GCCTTTGAAA | 1500 |
| TGTGAAAAGT TTGAATCATT TTCTTCATTT TAATTTCTTT GATTATTTTC | 1550 |
| ATATTTTCTC AATTGCAGAA TGAGATAAAA ACTACATACT GTCGACAAAT | 1600 |
| AAACTACTAT TGGAANGTTA AAATAATGTG TGTGTTGNAT GTTANGCCTA | 1650 |
| ATGGAANGGA TGNGGTTANG CAATTTATGA ACTGNNCGCT CTGTTCGCTT | 1700 |
| AAAANCCTTG GTTCCACCTT AANGGAANGG NCCGGCCATT | 1740 |

(2) INFORMATION FOR SEQ ID NO:13:

(i) SEQUENCE CHARACTERISTICS:
        (A) LENGTH:1666
        (B) TYPE:nucleic acid
        (C) STRANDEDNESS:double
        (D) TOPOLOGY:linear (xi) SEQUENCE DESCRIPTION:SEQ ID NO:13:

```
ATG GAA GCT CTT CTC AAG CCT TTT CCA TCT CTT TTA CTT TCC TCT          45
Met Glu Ala Leu Leu Lys Pro Phe Pro Ser Leu Leu Leu Ser Ser
              5                  10                  15

CCT ACA CCC CAT AGG TCT ATT TTC CAA CAA AAT CCC TCT TTT CTA          90
Pro Thr Pro His Arg Ser Ile Phe Gln Gln Asn Pro Ser Phe Leu
             20                  25                  30

AGT CCC ACC ACC AAA AAA AAA TCA AGA AAA TGT CTT CTT AGA AAC         135
Ser Pro Thr Thr Lys Lys Lys Ser Arg Lys Cys Leu Leu Arg Asn
             35                  40                  45

AAA AGT AGT AAA CTT TTT TGT AGC TTT CTT GAT TTA GCA CCC ACA         180
Lys Ser Ser Lys Leu Phe Cys Ser Phe Leu Asp Leu Ala Pro Thr
             50                  55                  60

TCA AAG CCA GAG TCT TTA GAT GTT AAC ATC TCA TGG GTT GAT CCT         225
Ser Lys Pro Glu Ser Leu Asp Val Asn Ile Ser Trp Val Asp Pro
             65                  70                  75

AAT TCG AAT CGG GCT CAA TTC GAC GTG ATC ATT ATC GGA GCT GGC         270
Asn Ser Asn Arg Ala Gln Phe Asp Val Ile Ile Ile Gly Ala Gly
             80                  85                  90

CCT GCT GGG CTC AGG CTA GCT GAA CAA GTT TCT AAA TAT GGT ATT         315
Pro Ala Gly Leu Arg Leu Ala Glu Gln Val Ser Lys Tyr Gly Ile
             95                 100                 105

AAG GTA TGT TGT GTT GAC CCT TCA CCA CTC TCC ATG TGG CCA AAT         360
Lys Val Cys Cys Val Asp Pro Ser Pro Leu Ser Met Trp Pro Asn
            110                 115                 120

AAT TAT GGT GTT TGG GTT GAT GAG TTT GAG AAT TTA GGA CTG GAA         405
Asn Tyr Gly Val Trp Val Asp Glu Phe Glu Asn Leu Gly Leu Glu
            125                 130                 135

AAT TGT TTA GAT CAT AAA TGG CCT ATG ACT TGT GTG CAT ATA AAT         450
Asn Cys Leu Asp His Lys Trp Pro Met Thr Cys Val His Ile Asn
            140                 145                 150

GAT AAC AAA ACT AAG TAT TTG GGA AGA CCA TAT GGT AGA GTT AGT         495
Asp Asn Lys Thr Lys Tyr Leu Gly Arg Pro Tyr Gly Arg Val Ser
            155                 160                 165

AGA AAG AAG CTG AAG TTG AAA TTG TTG AAT AGT TGT GTT GAG AAC         540
Arg Lys Lys Leu Lys Leu Lys Leu Leu Asn Ser Cys Val Glu Asn
            170                 175                 180
```

```
AGA GTG AAG TTT TAT AAA GCT AAG GTT TGG AAA GTG AAA CAT GAA                585
Arg Val Lys Phe Tyr Lys Ala Lys Val Trp Lys Val Glu His Glu
                185                 190                 195

GAA TTT GAG TCT TCA ATT GTT TGT GAT GAT GGT AAG AAG ATA AGA                630
Glu Phe Glu Ser Ser Ile Val Cys Asp Asp Gly Lys Lys Ile Arg
                200                 205                 210

GGT AGT TTG GTT GTG GAT GCA AGT GGT TTT GCT AGT GAT TTT ATA                675
Gly Ser Leu Val Val Asp Ala Ser Gly Phe Ala Ser Asp Phe Ile
                215                 220                 225

GAG TAT GAC AGG CCA AGA AAC CAT GGT TAT CAA ATT GCT CAT GGG                720
Glu Tyr Asp Arg Pro Arg Asn His Gly Tyr Gln Ile Ala His Gly
                230                 235                 240

GTT TTA GTA GAA GTT GAT AAT CAT CCA TTT GAT TTG GAT AAA ATG                765
Val Leu Val Glu Val Asp Asn His Pro Phe Asp Leu Asp Lys Met
                245                 250                 255

GTG CTT ATG GAT TGG AGG GAT TCT CAT TTG GGT AAT GAG CCA TAT                810
Val Leu Met Asp Trp Arg Asp Ser His Leu Gly Asn Glu Pro Tyr
                260                 265                 270

TTA AGG GTG AAT AAT GCT AAA GAA CCA ACA TTC TTG TAT GCA ATG                855
Leu Arg Val Asn Asn Ala Lys Glu Pro Thr Phe Leu Tyr Ala Met
                275                 280                 285

CCA TTT GAT AGA GAT TTG GTT TTC TTG GAA GAG ACT TCT TTG GTG                900
Pro Phe Asp Arg Asp Leu Val Phe Leu Glu Glu Thr Ser Leu Val
                290                 295                 300

AGT CGT CCT GTT TTA TCG TAT ATG GAA GTA AAA AGA AGG ATG GTG                945
Ser Arg Pro Val Leu Ser Tyr Met Glu Val Lys Arg Arg Met Val
                305                 310                 315

GCA AGA TTA AGG CAT TTG GGG ATC AAA GTG AAA AGT GTT ATT GAG                990
Ala Arg Leu Arg His Leu Gly Ile Lys Val Lys Ser Val Ile Glu
                320                 325                 330

GAA GAG AAA TGT GTG ATC CCT ATG GGA GGA CCA CTT CCG CGG ATT               1035
Glu Glu Lys Cys Val Ile Pro Met Gly Gly Pro Leu Pro Arg Ile
                335                 340                 345

CCT CAA AAT GTT ATG GCT ATT GGT GGG AAT TCA GGG ATA GTT CAT               1080
Pro Gln Asn Val Met Ala Ile Gly Gly Asn Ser Gly Ile Val His
                350                 355                 360

CCA TCA ACA GGG TAC ATG GTG GCT AGG AGC ATG GCT TTA GCA CCA               1125
Pro Ser Thr Gly Tyr Met Val Ala Arg Ser Met Ala Leu Ala Pro
                365                 370                 375

GTA CTA GCT GAA GCC ATC GTC GAG GGG CTT GGC TCA ACA AGA ATG               1170
Val Leu Ala Glu Ala Ile Val Glu Gly Leu Gly Ser Thr Arg Met
                380                 385                 390

ATA AGA GGG TCT CAA CTT TAC CAT AGA GTT TGG AAT GGT TTG TGG               1215
Ile Arg Gly Ser Gln Leu Tyr His Arg Val Trp Asn Gly Leu Trp
                395                 400                 405

CCT TTG GAT AGA AGA TGT GTT AGA GAA TGT TAT TCA TTT GGG ATG               1260
Pro Leu Asp Arg Arg Cys Val Arg Glu Cys Tyr Ser Phe Gly Met
                410                 415                 420

GAG ACA TTG TTG AAG CTT GAT TTG AAA GGG ACT AGG AGA TTG TTT               1305
Glu Thr Leu Leu Lys Leu Asp Leu Lys Gly Thr Arg Arg Leu Phe
                425                 430                 435

GAC GCT TTC TTT GAT CTT GAT CCT AAA TAC TGG CAA GGG TTC CTT               1350
Asp Ala Phe Phe Asp Leu Asp Pro Lys Tyr Trp Gln Gly Phe Leu
                440                 445                 450

TCT TCA AGA TTG TCT GTC AAA GAA CTT GGT TTA CTC AGC TTG TGT               1395
Ser Ser Arg Leu Ser Val Lys Glu Leu Gly Leu Leu Ser Leu Cys
                455                 460                 465

CTT TTC GGA CAT GGC TCA AAC ATG ACT AGG TTG GAT ATT GTT ACA               1440
Leu Phe Gly His Gly Ser Asn Met Thr Arg Leu Asp Ile Val Thr
```

-continued

```
              470             475             480
AAA TGT CCT CTT CCT TTG GTT AGA CTG ATT GGC AAT CTA GCA ATA        1485
Lys Cys Pro Leu Pro Leu Val Arg Leu Ile Gly Asn Leu Ala Ile
                     485             490             495

GAG AGC CTT TGA ATG TGA AAA GTT TGA ATC ATT TTC TTC ATT TTA        1530
Glu Ser Leu
        498

ATT TCT TTG ATT ATT TTC ATA TTT TCT CAA TTG CAA AAG TGA GAT        1575

AAG AGC TAC ATA CTG TCA ACA AAT AAA CTA CTA TTG GAA AGT AAA        1620

AAT ATG TGT TTG TTG TAT GTT ATT CTA ATG GAA TGG ATT TTG TAA        1665

A                                                                  1666
```

(2) INFORMATION FOR SEQ ID NO:14:

(i) SEQUENCE CHARACTERISTICS:
        (A) LENGTH:2876
        (B) TYPE:nucleic acid
        (C) STRANDEDNESS:double
        (D) TOPOLOGY:linear (xi) SEQUENCE DESCRIPTION:SEQ ID NO:14:

```
  G AAT TCT CTG AAA AGG AGC ACC ATA TTT GCC GCA CTG TGG TTC          43

ATA TTT CCA AGT ACA TTT AGA TGA ACT ATA TCA TCA GAT TGA AAG         88

GTT ATT GTA TAA TCA ATC CAG TGG ATT CTC GTT CTG GCA CCT TTA        133

GAA GTA CAT GTG CGG AAA AGA ATG ATA AGG TTT GTA TTG TTG TTG        178

ACA AAG CCT GTT GCC TTT CTC ATT TGT AAA TGT TCT GAA CGA CTC        223

CTA AAT TAC TCT TAA GGT GTA AGG TCT TCC GTG CCT GTT TGT AAA        268

TAT AAT GCT GTG CCG TGA CTT ACC TTT TGT ACC ATT TGT TCA AAT        313

GTA TGG CCT GAA CAC CAG GGT TGT CAA AAA TGT CTC ATG CCC GTT        358

TTA TTG GTC TGA AAA TGG CGT GAT GCC AAA TTC TGC CGC TCC ACA        403

GTG AGC ATT TCG ATC TAC TGG AAA TTG ACC AAC TTA TTT TAT CAC        448

TTG ATA ACT AAA CAA AAT CCT ATT AAC TTT AAT CAT ACA TTG TAT        493

TTA TAC CGA AAA ATT TAT GCA TAA CTC ATT AAA TTA CCT TTT TTA        538

GCA GTC AAA TTC TAA ATC AGT TTC TAA TTT ATC AAA ATG GCT TTT        583

ATA GGG TCC CAT TTC CAC TAA TAT ACC TGC CGT CCA TGC ACT GAC        628

TAC AAA ACA AAT ACC TCA CTA TGT TTG TTA GTG CTT GGT AAT ATA        673

AAA CCT TTT CTT TTA TGA GAA AGT TCA CCG AGA ATA ATT TTC TAT        718

TTG TGG CAT AAT AGT ATA TAG TGC AGA TTG ACA AGA ATT TAA TTT        763

TGC AGT TGG GCA CAT GAA CAA TTT TCC TCA AAG TTG TAG AAA GTA        808

CTT TTC ATT TTC TTG TCA CCG AAA ATT ATT TAT AAT TGA AAT TAA        853

AAC CGA ATG AGC TGC AAG ATT CAA GTC GAA TTT TCA AAA GAA TTG        898

ACC AAG AAA AAA TTC AAA AAT ATC CCC CAC CCC CTA CCA AAC ACA        943

TCC TAA AGT GAG GTA TAG ACT GGG ACT GGG ATT GGG AAA AGG GTA        988

AAA TGC TTT CAC TAG CTT AGC AAA GAT TCC ACT TTG TTA GCT ATC       1033

TTT CTT TCT CAT TTC CTT TTT TCT TTT TCT TTT TTT TGT TAT ATA       1078

AGC CAA AGT AGG TAC CCA AAA GCA TCA ATA TTT TGT ATT GCT TGG       1123
```

```
TGA TTC CTC TGT AGT CCA GTA TTT CAT TTT CTA CAA GTT CCA CCT                                              1168

CCC TCC ATA ATT AAC CAT TAT CAA TCT TAT ACA TTC TCT ATA ATG                                              1213
                                                                Met

GAA ACT CTT CTC AAG CCT TTT CCA TCT CTT TTA CTT TCC TCT CCT                                              1258
Glu Thr Leu Leu Lys Pro Phe Pro Ser Leu Leu Leu Ser Ser Pro
                 5                  10                  15

ACA CCC CAT AGG TCT ATT TTC CAA CAA AAT CCC TCT TTT CTA AGT                                              1303
Thr Pro His Arg Ser Ile Phe Gln Gln Asn Pro Ser Phe Leu Ser
                20                  25                  30

CCC ACC ACC AAA AAA AAA TCA AGA AAA TGT CTT CTT AGA AAC AAA                                              1348
Pro Thr Thr Lys Lys Lys Ser Arg Lys Cys Leu Leu Arg Asn Lys
                35                  40                  45

AGT AGT AAA CTT TTT TGT AGC TTT CTT GAT TTA GCA CCC ACA TCA                                              1393
Ser Ser Lys Leu Phe Cys Ser Phe Leu Asp Leu Ala Pro Thr Ser
                50                  55                  60

AAG CCA GAG TCT TTA GAT GTT AAC ATC TCA TGG GTT GAT CCT AAT                                              1438
Lys Pro Glu Ser Leu Asp Val Asn Ile Ser Trp Val Asp Pro Asn
                65                  70                  75

TCG AAT CGG GCT CAA TTC GAC GTG ATC ATT ATC GGA GCT GGC CCT                                              1483
Ser Asn Arg Ala Gln Phe Asp Val Ile Ile Ile Gly Ala Gly Pro
                80                  85                  90

GCT GGG CTC AGG CTA GCT GAA CAA GTT TCT AAA TAT GGT ATT AAG                                              1528
Ala Gly Leu Arg Leu Ala Glu Gln Val Ser Lys Tyr Gly Ile Lys
                95                 100                 105

GTA TGT TGT GTT GAC CCT TCA CCA CTC TCC ATG TGG CCA AAT AAT                                              1573
Val Cys Cys Val Asp Pro Ser Pro Leu Ser Met Trp Pro Asn Asn
               110                 115                 120

TAT GGT GTT TGG GTT GAT GAG TTT GAG AAT TTA GGA CTG GAA AAT                                              1618
Tyr Gly Val Trp Val Asp Glu Phe Glu Asn Leu Gly Leu Glu Asn
               125                 130                 135

TGT TTA GAT CAT AAA TGG CCT ATG ACT TGT GTG CAT ATA AAT GAT                                              1663
Cys Leu Asp His Lys Trp Pro Met Thr Cys Val His Ile Asn Asp
               140                 145                 150

AAC AAA ACT AAG TAT TTG GGA AGA CCA TAT GGT AGA GTT AGT AGA                                              1708
Asn Lys Thr Lys Tyr Leu Gly Arg Pro Tyr Gly Arg Val Ser Arg
               155                 160                 165

AAG AAG CTG AAG TTG AAA TTG TTG AAT AGT TGT GTT GAG AAC AGA                                              1753
Lys Lys Leu Lys Leu Lys Leu Leu Asn Ser Cys Val Glu Asn Arg
               170                 175                 180

GTG AAG TTT TAT AAA GCT AAG GTT TGG AAA GTG GAA CAT GAA GAA                                              1798
Val Lys Phe Tyr Lys Ala Lys Val Trp Lys Val Glu His Glu Glu
               185                 190                 195

TTT GAG TCT TCA ATT GTT TGT GAT GAT GGT AAG AAG ATA AGA GGT                                              1843
Phe Glu Ser Ser Ile Val Cys Asp Asp Gly Lys Lys Ile Arg Gly
               200                 205                 210

AGT TTG GTT GTG GAT GCA AGT GGT TTT GCT AGT GAT TTT ATA GAG                                              1888
Ser Leu Val Val Asp Ala Ser Gly Phe Ala Ser Asp Phe Ile Glu
               215                 220                 225

TAT GAC AGG CCA AGA AAC CAT GGT TAT CAA ATT GCT CAT GGG GTT                                              1933
Tyr Asp Arg Pro Arg Asn His Gly Tyr Gln Ile Ala His Gly Val
               230                 235                 240

TTA GTA GAA GTT GAT AAT CAT CCA TTT GAT TTG GAT AAA ATG GTG                                              1978
Leu Val Glu Val Asp Asn His Pro Phe Asp Leu Asp Lys Met Val
               245                 250                 255

CTT ATG GAT TGG AGG GAT TCT CAT TTG GGT AAT GAG CCA TAT TTA                                              2023
Leu Met Asp Trp Arg Asp Ser His Leu Gly Asn Glu Pro Tyr Leu
               260                 265                 270

AGG GTG AAT AAT GCT AAA GAA CCA ACA TTC TTG TAT GCA ATG CCA                                              2068
Arg Val Asn Asn Ala Lys Glu Pro Thr Phe Leu Tyr Ala Met Pro
```

-continued

```
                    275                 280                 285
TTT GAT AGA GAT TTG GTT TTC TTG GAA GAG ACT TCT TTG GTG AGT          2113
Phe Asp Arg Asp Leu Val Phe Leu Glu Glu Thr Ser Leu Val Ser
                    290                 295                 300

CGT CCT GTT TTA TCG TAT ATG GAA GTA AAA AGA AGG ATG GTG GCA          2158
Arg Pro Val Leu Ser Tyr Met Glu Val Lys Arg Arg Met Val Ala
                    305                 310                 315

AGA TTA AGG CAT TTG GGG ATC AAA GTG AAA AGT GTT ATT GAG GAA          2203
Arg Leu Arg His Leu Gly Ile Lys Val Lys Ser Val Ile Glu Glu
                    320                 325                 330

GAG AAA TGT GTG ATC CCT ATG GGA GGA CCA CTT CCG CGG ATT CCT          2248
Glu Lys Cys Val Ile Pro Met Gly Gly Pro Leu Pro Arg Ile Pro
                    335                 340                 345

CAA AAT GTT ATG GCT ATT GGT GGG AAT TCA GGG ATA GTT CAT CCA          2293
Gln Asn Val Met Ala Ile Gly Gly Asn Ser Gly Ile Val His Pro
                    350                 355                 360

TCA ACA GGG TAC ATG GTG GCT AGG AGC ATG GCT TTA GCA CCA GTA          2338
Ser Thr Gly Tyr Met Val Ala Arg Ser Met Ala Leu Ala Pro Val
                    365                 370                 375

CTA GCT GAA GCC ATC GTC GAG GGG CTT GGC TCA ACA AGA ATG ATA          2383
Leu Ala Glu Ala Ile Val Glu Gly Leu Gly Ser Thr Arg Met Ile
                    380                 385                 390

AGA GGG TCT CAA CTT TAC CAT AGA GTT TGG AAT GGT TTG TGG CCT          2428
Arg Gly Ser Gln Leu Tyr His Arg Val Trp Asn Gly Leu Trp Pro
                    395                 400                 405

TTG GAT AGA AGA TGT GTT AGA GAA TGT TAT TCA TTT GGG ATG GAG          2473
Leu Asp Arg Arg Cys Val Arg Glu Cys Tyr Ser Phe Gly Met Glu
                    410                 415                 420

ACA TTG TTG AAG CTT GAT TTG AAA GGG ACT AGG AGA TTG TTT GAC          2518
Thr Leu Leu Lys Leu Asp Leu Lys Gly Thr Arg Arg Leu Phe Asp
                    425                 430                 435

GCT TTC TTT GAT CTT GAT CCT AAA TAC TGG CAA GGG TTC CTT TCT          2563
Ala Phe Phe Asp Leu Asp Pro Lys Tyr Trp Gln Gly Phe Leu Ser
                    440                 445                 450

TCA AGA TTG TCT GTC AAA GAA CTT GGT TTA CTC AGC TTG TGT CTT          2608
Ser Arg Leu Ser Val Lys Glu Leu Gly Leu Leu Ser Leu Cys Leu
                    455                 460                 465

TTC GGA CAT GGC TCA AAC ATG ACT AGG TTG GAT ATT GTT ACA AAA          2653
Phe Gly His Gly Ser Asn Met Thr Arg Leu Asp Ile Val Thr Lys
                    470                 475                 480

TGT CCT CTT CCT TTG GTT AGA CTG ATT GGC AAT CTA GCA ATA GAG          2698
Cys Pro Leu Pro Leu Val Arg Leu Ile Gly Asn Leu Ala Ile Glu
                    485                 490                 495

AGC CTT TGA ATG TGA AAA GTT TGA ATC ATT TTC TTC ATT TTA ATT          2743
Ser Leu
    498

TCT TTG ATT ATT TTC ATA TTT TCT CAA TTG CAA AAG TGA GAT AAG          2788

AGC TAC ATA CTG TCA ACA AAT AAA CTA CTA TTG GAA AGT TAA AAT          2833

ATG TGT TTG TTG TAT GTT ATT CTA ATG GAA TGG ATT TGT AAA             2876
```

(2) INFORMATION FOR SEQ ID NO:15:

(i) SEQUENCE CHARACTERISTICS:
        (A) LENGTH:3265
        (B) TYPE:nucleic acid
        (C) STRANDEDNESS:double
        (D) TOPOLOGY:linear (xi) SEQUENCE DESCRIPTION:SEQ ID NO:15:

-continued

| | |
|---|---|
| ATC TCA TTG TAT AGC TTG TCT TTT GTT TCA GTC GTC TTA GGC TTG | 45 |
| GGT TAG TTG GTG TTG CTG TTT CAT ACT TCT ATC AAC CTT GTG TGA | 90 |
| GTT CCT TTA TAA AAT ATG ACT GTT GGA GGA AGT AAT TTA CCT TTA | 135 |
| GTT CGA CTA CAT CAA GAT TTG CAT CAT TCT CGT CCA AGA AAT CTT | 180 |
| AGT TTG AAG CCT TTT GGT CTG GTA TAT TTG TCA ATC TGA GCT CCG | 225 |
| CAA CTT TCT CAT GAC AGG GGT TTG TTG ACA TGC CTG ATT GTG CTC | 270 |
| TTC CTT TAC TTG ATA ATT GCT GCT TGT TGC GGA GGC ATC ACT CTA | 315 |
| CCT TCC TGC AGA TCA TGA ATT CTC TGA AAA GGA GCA CCA TAT TTG | 360 |
| CCG CAC TGT GGT TCA TAT TTC CAA TTA CAT TTA GAT GAA CTA TAT | 405 |
| CAT CAG GAG TGA AAG GTT ATT GTA TAA TCA ATC CAG TGG ATT CTC | 450 |
| GTT CTG GCA CCT TTA GAA GTA CAT GTG CGG AAA AGA ATG ATA AGG | 495 |
| TTT GTA TTG TTG TTG ACA AGG CCT GTT GCC TTT CTC ATT TGT AAA | 540 |
| TGT TCT GAA CGA CTC CTA AAT TAC TCT TAA AGT GTA AGG TCT TCC | 585 |
| GTG CCT GTT TGT ATA TAT AAT GCT GTG CCG TGA CTT ACC TTT TGT | 630 |
| ACC ATT TGT TCA AAT GTA TGG CCT GGA CAC TAG GGT TGT CAA AAA | 675 |
| TGT CTC ATG ACT TCA CCC TTC TTT CTT GTC TTG GTG CCC GTT TTA | 720 |
| TTG GTC TGA GAA CGG CGT GAT GCC AAA TTC TGC CGC TCC ACA GTG | 765 |
| AGC ATT TCG ATC TAC TGG AAA TTG ACC AAC TTA TTT TAT CAC TTG | 810 |
| ATA ACT AGA GTC TGG GTT CAA ACA AAA TCC AAT AAC TTC AAT CAT | 855 |
| ACA TTG TAT TTA TAT TGA AAA AAT TAT GCA CAA CTC AGT AAA TTA | 900 |
| CCT TTT TTT GCA GTC AAA AAT TCT AGA TCA GTT TCT AAT TAA TCA | 945 |
| AAA TGG CCT TTA TAG GGT CCC AGT TCC ATT AAT ATA CCT GCC GTC | 990 |
| CAT GCA CTG ATT ACA AGA CAA ATA CCT CAC TAT GTT TGT TAG TGC | 1035 |
| TTG GTA ATA TAA AAC CTT TTC TTT TAT GAG AAA GTT CAC CGA AAA | 1080 |
| TAA TTT TCT ATT TGT GGC ATA ACT AGT ATC GAA GTA TAT AGT GCA | 1125 |
| GAT TGA CAA GAA TTT AAT TTT GCA GTT GGG CAC ATG AAC AAT TTT | 1170 |
| CCT CAA AGT TGT AGA AAA TAT TTT TCA TTT TCT TGT CAC CGA AAA | 1215 |
| TTA TTT ATA ATT GAA ATT GAA ACC GAA TGA GCT GCA AGA CTC GAG | 1260 |
| TCG AAT TTC AAA AAA ATT GAC CAA CTA AAT ATG AAA AAA TCC GAA | 1305 |
| TAT ATC CCC CAC CCC CTA CCA AAC ACA TCC TAA AGT GAG GTA TAG | 1350 |
| ACT GGG ACT GGG ATT GGG AAA AGG GTA AAA TGC TTT CAC TAG CTT | 1395 |
| AGC AAA GAT TCC ACT TTG TTA GCT ATC TTT CTT TCT CAT TTC CTT | 1440 |
| TTT TCT TTT TCT TTT TTT TGT TAT ATA AGC CAA AGT AGG TAC CCA | 1485 |
| AAA GCA TCA ATA TTT TGT ATT GCT TGG TGA TTC CTC TTT ACT CCA | 1530 |
| GTA TTT CAT TTT CTA CAA GTT CCA CCT CCC TCC ATA ATT AAC CAT | 1575 |
| TAT CAA TCT TAT ACA TTT TCT ATA ATG GAA ACT CTT CTC AAG CCT<br>          Met Glu Thr Leu Leu Lys Pro<br>                5 | 1620 |
| TTT CCA TCT CTT TTA CTT TCC TCT CCT ACA CCC TAT AGG TCT ATT<br>Phe Pro Ser Leu Leu Leu Ser Ser Pro Thr Pro Tyr Arg Ser Ile<br>  10       15       20 | 1665 |
| GTC CAA CAA AAT CCT TCT TTT CTA AGT CCC ACC ACC CAA AAA AAA | 1710 |

-continued

| | | |
|---|---|---|
| Val Gln Gln Asn Pro Ser Phe Leu Ser Pro Thr Thr Gln Lys Lys<br>             25                        30                     35 | | |
| TCA AGA AAA TGT CTT CTT AGA AAC AAA AGT AGT AAA CTT TTT TGT<br>Ser Arg Lys Cys Leu Leu Arg Asn Lys Ser Ser Lys Leu Phe Cys<br>        40                        45                       50 | 1755 | |
| AGC TTT CTT GAT TTA GCA CCC ACA TCA AAG CCA GAG TCT TTA AAT<br>Ser Phe Leu Asp Leu Ala Pro Thr Ser Lys Pro Glu Ser Leu Asn<br>        55                        60                       65 | 1800 | |
| GTT AAC ATC TCA TGG GTT GAT CCT AAT TCT GGT CGG GCT CAA TTC<br>Val Asn Ile Ser Trp Val Asp Pro Asn Ser Gly Arg Ala Gln Phe<br>        70                        75                       80 | 1845 | |
| GAC GTG ATC ATT ATC GGA GCT GGC CCT GCT GGG CTC AGG TTA GCT<br>Asp Val Ile Ile Ile Gly Ala Gly Pro Ala Gly Leu Arg Leu Ala<br>        85                        90                       95 | 1890 | |
| GAA CAA GTT TCT AAA TAT GGT ATT AAG GTA TGT TGT GTT GAC CCT<br>Glu Gln Val Ser Lys Tyr Gly Ile Lys Val Cys Cys Val Asp Pro<br>       100                      105                   110 | 1935 | |
| TCA CCA CTC TCC ATG TGG CCA AAT AAT TAT GGT GTT TGG GTT GAT<br>Ser Pro Leu Ser Met Trp Pro Asn Asn Tyr Gly Val Trp Val Asp<br>       115                      120                   125 | 1980 | |
| GAG TTT GAG AAT TTA GGA CTG GAA GAT TGT TTA GAT CAT AAA TGG<br>Glu Phe Glu Asn Leu Gly Leu Glu Asp Cys Leu Asp His Lys Trp<br>       130                      135                   140 | 2025 | |
| CCT ATG ACT TGT GTG CAT ATA AAT GAT AAC AAG ACT AAG TAT TTG<br>Pro Met Thr Cys Val His Ile Asn Asp Asn Lys Thr Lys Tyr Leu<br>       145                      150                   155 | 2070 | |
| GGA AGA CCA TAT GGT AGA GTT AGT AGA AAG AAG CTG AAG TTG AAA<br>Gly Arg Pro Tyr Gly Arg Val Ser Arg Lys Lys Leu Lys Leu Lys<br>       160                      165                   170 | 2115 | |
| TTG TTG AAC AGT TGT GTT GAG AAC AGA GTG AAG TTT TAT AAA GCT<br>Leu Leu Asn Ser Cys Val Glu Asn Arg Val Lys Phe Tyr Lys Ala<br>       175                      180                   185 | 2160 | |
| AAG GTT TGG AAA GTG GAA CAT GAA GAA TTT GAG TCT TCA ATT GTT<br>Lys Val Trp Lys Val Glu His Glu Glu Phe Glu Ser Ser Ile Val<br>       190                      195                   200 | 2205 | |
| TGT GAT GAT GGT AAG AAG ATA AGA GGT AGT TTG GTT GTG GAT GCA<br>Cys Asp Asp Gly Lys Lys Ile Arg Gly Ser Leu Val Val Asp Ala<br>       205                      210                   215 | 2250 | |
| AGT GGT TTT GCT AGT GAT TTT ATA GAG TAT GAC AAG CCA AGA AAC<br>Ser Gly Phe Ala Ser Asp Phe Ile Glu Tyr Asp Lys Pro Arg Asn<br>       220                      225                   230 | 2295 | |
| CAT GGT TAT CAA ATT GCT CAT GGG GTT TTA GTA GAA GTT GAT AAT<br>His Gly Tyr Gln Ile Ala His Gly Val Leu Val Glu Val Asp Asn<br>       235                      240                   245 | 2340 | |
| CAT CCA TTT GAT TTG GAT AAA ATG GTG CTT ATG GAT TGG AGG GAT<br>His Pro Phe Asp Leu Asp Lys Met Val Leu Met Asp Trp Arg Asp<br>       250                      255                   260 | 2385 | |
| TCT CAT TTA GGT AAT GAG CCA TAT TTA AGG GTG AAT AAT GCT AAA<br>Ser His Leu Gly Asn Glu Pro Tyr Leu Arg Val Asn Asn Ala Lys<br>       265                      270                   275 | 2430 | |
| GAA CCA ACA TTC TTG TAT GCA ATG CCA TTT GAT AGA AAT TTG GTT<br>Glu Pro Thr Phe Leu Tyr Ala Met Pro Phe Asp Arg Asn Leu Val<br>       280                      285                   290 | 2475 | |
| TTC TTG GAA GAG ACT TCT TTG GTG AGT CGT CCT GTG TTA TCG TAT<br>Phe Leu Glu Glu Thr Ser Leu Val Ser Arg Pro Val Leu Ser Tyr<br>       295                      300                   305 | 2520 | |
| ATG GAA GTA AAA AGA AGG ATG GTG GCA AGA TTA AGG CAT TTG GGG<br>Met Glu Val Lys Arg Arg Met Val Ala Arg Leu Arg His Leu Gly<br>       310                      315                   320 | 2565 | |

```
ATC AAA GTG AGA AGT GTT ATT GAG GAA GAG AAA TGT GTG ATC CCT        2610
Ile Lys Val Arg Ser Val Ile Glu Glu Glu Lys Cys Val Ile Pro
    325                 330                 335

ATG GGA GGA CCA CTT CCG CGG ATT CCT CAA AAT GTT ATG GCT ATT        2655
Met Gly Gly Pro Leu Pro Arg Ile Pro Gln Asn Val Met Ala Ile
            340                 345                 350

GGT GGG AAT TCA GGG ATA GTT CAT CCA TCA ACG GGG TAC ATG GTG        2700
Gly Gly Asn Ser Gly Ile Val His Pro Ser Thr Gly Tyr Met Val
        355                 360                 365

GCT AGG AGC ATG GCT TTA GCA CCA GTA CTA GCT GAA GCC ATC GTC        2745
Ala Arg Ser Met Ala Leu Ala Pro Val Leu Ala Glu Ala Ile Val
    370                 375                 380

GAG GGG CTT GGC TCA ACA AGA ATG ATA AGA GGG TCT CAA CTT TAC        2790
Glu Gly Leu Gly Ser Thr Arg Met Ile Arg Gly Ser Gln Leu Tyr
            385                 390                 395

CAT AGA GTT TGG AAT GGT TTG TGG CCT TTG GAT AGA AGA TGT GTT        2835
His Arg Val Trp Asn Gly Leu Trp Pro Leu Asp Arg Arg Cys Val
        400                 405                 410

AGA GAA TGT TAT TCA TTT GGG ATG GAG ACA TTG TTG AAG CTT GAT        2880
Arg Glu Cys Tyr Ser Phe Gly Met Glu Thr Leu Leu Lys Leu Asp
    415                 420                 425

TTG AAA GGG ACT AGG AGA TTG TTT GAC GCT TTC TTT GAT CTT GAT        2925
Leu Lys Gly Thr Arg Arg Leu Phe Asp Ala Phe Phe Asp Leu Asp
            430                 435                 440

CCT AAA TAC TGG CAA GGG TTC CTT TCT TCA AGA TTG TCT GTC AAA        2970
Pro Lys Tyr Trp Gln Gly Phe Leu Ser Ser Arg Leu Ser Val Lys
        445                 450                 455

GAA CTT GGT TTA CTC AGC TTG TGT CTT TTC GGA CAT GGC TCA AAT        3015
Glu Leu Gly Leu Leu Ser Leu Cys Leu Phe Gly His Gly Ser Asn
    460                 465                 470

TTG ACT AGG TTG GAT ATT GTT ACA AAA TGT CCT GTT CCT TTG GTT        3060
Leu Thr Arg Leu Asp Ile Val Thr Lys Cys Pro Val Pro Leu Val
            475                 480                 485

AGA CTG ATT GGC AAT CTA GCA GTA GAG AGC CTT TGA ATG TGA AAA        3105
Arg Leu Ile Gly Asn Leu Ala Val Glu Ser Leu
    490                 495         498

GTT TGA ATC ATT TCT TTT ATT TTA ATT TCT TTG ATT ATT TTC ATA        3150

TTT TCT CAA TGC AAA AGT GAG AGA AGA CTA TAC ACT GTC AAC AAA        3195

TAA ACT ACT ATT GGA AAG TTA AAA TAA TGT GTG TGT TGT ATG TTA        3240

TGC TAA TGG AAT GGA TTG GTG TAA A                                 3265
```

(2) INFORMATION FOR SEQ ID NO:16:

(i) SEQUENCE CHARACTERISTICS:
    (A) LENGTH:1740
    (B) TYPE:nucleic acid
    (C) STRANDEDNESS:double
    (D) TOPOLOGY:linear (xi) SEQUENCE DESCRIPTION:SEQ ID NO:16:

```
ATG GAA GCT CTT CTC AAG CCT TTT CCA TCT CTT TTA CTT TCC TCT          45
Met Glu Ala Leu Leu Lys Pro Phe Pro Ser Leu Leu Leu Ser Ser
            5                   10                  15

CCT ACA CCC TAT AGG TCT ATT GTC CAA CAA AAT CCT TCT TTT CTA          90
Pro Thr Pro Tyr Arg Ser Ile Val Gln Gln Asn Pro Ser Phe Leu
        20                  25                  30

AGT CCC ACC ACC AAA AAA AAT CAA GAA AAT GTC TTC TTA GAA ACA         135
Ser Pro Thr Thr Lys Lys Asn Gln Glu Asn Val Phe Leu Glu Thr
    35                  40                  45
```

```
AAA GTA GTA AAC TTT TTT GTA GCT TTC TTG ATT TAG CAC CCA CAT        180
Lys Val Val Asn Phe Phe Val Ala Phe Leu Ile
                50                  55  56

CAA AGC CAG AGT CTT TAA ATG TTA ACA TCT CAT GGG TTG ATC CTA        225

ATT CGA ATC GGG CTC AAT TCG ACG TGA TCA TTA TCG AGC TGG CC         270

CTG CTG GGC TCA GGC TAG CTG AAC AAG TTT CTA AAT ATG GTA TTA        315

AGG TAT GTT GTG TTG ACC CTT CAC CAC TCT CCA TGT GGC AAA TA         360

ATT ATG GTG TTT GGG TTG ATG AGT TTG AGA ATT TAG GAC TGG AAA        405

ATT GTT TAG ATC ATA AAT GGC CTA TGA CTT GTG TGC ATA TAA ATG        450

ATA ACA AAA CTA AGT ATT TGG GAA GAC CAT ATG GTA GAG TTA GTA        495

GAA AGA AGC TGA AGT TGA AAT TGT TGA ATA GTT GTG TTG AGA ACA        540

GAG TGA AGT TTT ATA AAG CTA AGG TTT GGA AAG TGG AAC ATG AAG        585

AAT TTG AGT CTT CAA TTG TTT GTG ATG ATG GTA AGA AGA TAA GAG        630

GTA GTT TGG TTG TGG ATG CAA GTG GTT TGC TAG TGA TTT TAG            675

AGT ATG ACA GGC CAA GAA ACC ATG GTT ATC AAA TTG CTC ATG GGG        720

TTT TAG TAG AAG TTG ATA ATC ATC CAT TTG ATT GGA ATA AAA TGG        765

TGC TTA TGG ATT GGA GGG ATT CTC ATT TGG GTA ATG AGC CAT ATT        810

TAA GGG TGA ATA ATG CTA AAG AAC CAA CAT TCT TGT ATG CAA TGC        855

CAT TTG ATA GAG ATT TGG TTT TCT TGG AAG AGA CTT CTT TGG TGA        900

GTC GTC CTG TGT TAT CGT ATA TGG AAG TAA AAA GAA GGA TGG TGG        945

CAA GAT TAA GGC ATT TGG GGA TCA AAG TGA AAA GTG TTA TTG AGG        990

AAG AGA AAT GTG TGA TCC CTA TGG GAG GAC CAC TTC CGC GGA TTC        1035

CTC AAA ATG TTA TGG CTA TTG GTG GGA ATT CAG GGA TAG TTC ATC        1080

CAT CAA CAG GGT ACA TGG TGG CTA GGA GCA TGG CTT TAG CAC CAG        1125

TAC TAG CTG AAG CCA TCG TCG AGG GGC TTG GCT CAA CAA GAA TGA        1170

TAA GAG GGT CTC AAC TTT ACC ATA GAG TTT GGA ATG GTT TGT GGC        1215

CTT TGG ATA GAA GAT GTG TTA GAG AAT GTT ATT CAT TTG GGA TGG        1260

AGA CAT TGT TGA AGC TTG ATT TGA AAG GGA CTA GGA GAT TGT TTG        1305

ACG CTT TCT TTG ATC TTG ATC CTA AAT ACT GGC AAG GGT TCC TTT        1350

CTT CAA GAT TGT CTG TCA AAG AAA CTT GGT TTA CTC AGC TTG TGT        1395

CTT TTC GGA CAT GGC TCA AAC ATG ACT AGG TTG GGA TAT TGT TAC        1440

AAA ATG TCC TCT TCC TTT GGT TAG ACT GAT TGG CAA TCT AGC AAT        1485

AGA GAG CCT TTG AAA TGT GAA AAG TTT GAA TCA TTT TCT TCA TTT        1530

TAA TTT CTT TGA TTA TTT TCA TAT TTT CTC AAT TGC AGA ATG AGA        1575

TAA AAA CTA CAT ACT GTC GAC AAA TAA ACT ACT ATT GGA ANG TTA        1620

AAA TAA TGT GTG TGT TGN ATG TTA NGC CTA ATG GAA NGG ATG NGG        1665

TTA NGC AAT TTA TGA ACT GNN CGC TCT GTT CGC TTA AAA NCC TTG        1710

GTT CCA CCT TAA NGG AAN GGN CCG GCC ATT                            1740

(2) INFORMATION FOR SEQ ID NO:17:

(i) SEQUENCE CHARACTERISTICS:
        (A) LENGTH:498
```

(B) TYPE:amino acid
        (C) STRANDEDNESS:single
        (D) TOPOLOGY:linear (xi) SEQUENCE DESCRIPTION:SEQ ID NO:17:

```
Met Glu Ala Leu Leu Lys Pro Phe Pro Ser Leu Leu Ser Ser
                5                  10                  15
Pro Thr Pro His Arg Ser Ile Phe Gln Gln Asn Pro Ser Phe Leu
            20                  25                  30
Ser Pro Thr Thr Lys Lys Ser Arg Lys Cys Leu Leu Arg Asn
            35                  40                  45
Lys Ser Ser Lys Leu Phe Cys Ser Phe Leu Asp Leu Ala Pro Thr
            50                  55                  60
Ser Lys Pro Glu Ser Leu Asp Val Asn Ile Ser Trp Val Asp Pro
            65                  70                  76
Asn Ser Asn Arg Ala Gln Phe Asp Val Ile Ile Ile Gly Ala Gly
            80                  85                  90
Pro Ala Gly Leu Arg Leu Ala Glu Gln Val Ser Lys Tyr Gly Ile
            95                  100                 105
Lys Val Cys Cys Val Asp Pro Ser Pro Leu Ser Met Trp Pro Asn
            110                 115                 120
Asn Tyr Gly Val Trp Val Asp Glu Phe Glu Asn Leu Gly Leu Glu
            125                 130                 135
Asn Cys Leu Asp His Lys Trp Pro Met Thr Cys Val His Ile Asn
            140                 145                 150
Asp Asn Lys Thr Lys Tyr Leu Gly Arg Pro Tyr Gly Arg Val Ser
            155                 160                 165
Arg Lys Lys Leu Lys Leu Lys Leu Leu Asn Ser Cys Val Glu Asn
            170                 175                 180
Arg Val Lys Phe Tyr Lys Ala Lys Val Trp Lys Val Glu His Glu
            185                 190                 195
Glu Phe Glu Ser Ser Ile Val Cys Asp Asp Gly Lys Lys Ile Arg
            200                 205                 210
Gly Ser Leu Val Val Asp Ala Ser Gly Phe Ala Ser Asp Phe Ile
            215                 220                 225
Glu Tyr Asp Arg Pro Arg Asn His Gly Tyr Gln Ile Ala His Gly
            230                 235                 240
Val Leu Val Glu Val Asp Asn His Pro Phe Asp Leu Asp Lys Met
            245                 250                 255
Val Leu Met Asp Trp Arg Asp Ser His Leu Gly Asn Glu Pro Tyr
            260                 265                 270
Leu Arg Val Asn Asn Ala Lys Glu Pro Thr Phe Leu Tyr Ala Met
            275                 280                 285
Pro Phe Asp Arg Asp Leu Val Phe Leu Glu Glu Thr Ser Leu Val
            290                 295                 300
Ser Arg Pro Val Leu Ser Tyr Met Glu Val Lys Arg Arg Met Val
            305                 310                 315
Ala Arg Leu Arg His Leu Gly Ile Lys Val Lys Ser Val Ile Glu
            320                 325                 330
Glu Glu Lys Cys Val Ile Pro Met Gly Gly Pro Leu Pro Arg Ile
            335                 340                 345
Pro Gln Asn Val Met Ala Ile Gly Gly Asn Ser Gly Ile Val His
            350                 355                 360
Pro Ser Thr Gly Tyr Met Val Ala Arg Ser Met Ala Leu Ala Pro
```

-continued

```
                    365                 370                 375
Val Leu Ala Glu Ala Ile Val Glu Gly Leu Gly Ser Thr Arg Met
                380                 385                 390
Ile Arg Gly Ser Gln Leu Tyr His Arg Val Trp Asn Gly Leu Trp
                395                 400                 405
Pro Leu Asp Arg Arg Cys Val Arg Glu Cys Tyr Ser Phe Gly Met
                410                 415                 420
Glu Thr Leu Leu Lys Leu Asp Leu Lys Gly Thr Arg Arg Leu Phe
                425                 430                 435
Asp Ala Phe Phe Asp Leu Asp Pro Lys Tyr Trp Gln Gly Phe Leu
                440                 445                 450
Ser Ser Arg Leu Ser Val Lys Glu Leu Gly Leu Leu Ser Leu Cys
                455                 460                 465
Leu Phe Gly His Gly Ser Asn Met Thr Arg Leu Asp Ile Val Thr
                470                 475                 480
Lys Cys Pro Leu Pro Leu Val Arg Leu Ile Gly Asn Leu Ala Ile
                485                 490                 495
Glu Ser Leu
        498
```

(2) INFORMATION FOR SEQ ID NO:18:

(i) SEQUENCE CHARACTERISTICS:
        (A) LENGTH:498
        (B) TYPE:amino acid
        (C) STRANDEDNESS:single
        (D) TOPOLOGY:linear (xi) SEQUENCE DESCRIPTION:SEQ ID NO:18:

```
Met Glu Ala Leu Leu Lys Pro Phe Pro Ser Leu Leu Leu Ser Ser
                 5                  10                  15
Pro Thr Pro His Arg Ser Ile Phe Gln Gln Asn Pro Ser Phe Leu
                20                  25                  30
Ser Pro Thr Thr Lys Lys Lys Ser Arg Lys Cys Leu Leu Arg Asn
                35                  40                  45
Lys Ser Ser Lys Leu Phe Cys Ser Phe Leu Asp Leu Ala Pro Thr
                50                  55                  60
Ser Lys Pro Glu Ser Leu Asp Val Asn Ile Ser Trp Val Asp Pro
                65                  70                  76
Asn Ser Asn Arg Ala Gln Phe Asp Val Ile Ile Gly Ala Gly
                80                  85                  90
Pro Ala Gly Leu Arg Leu Ala Glu Gln Val Ser Lys Tyr Gly Ile
                95                 100                 105
Lys Val Cys Cys Val Asp Pro Ser Pro Leu Ser Met Trp Pro Asn
               110                 115                 120
Asn Tyr Gly Val Trp Val Asp Glu Phe Glu Asn Leu Gly Leu Glu
               125                 130                 135
Asn Cys Leu Asp His Lys Trp Pro Met Thr Cys Val His Ile Asn
               140                 145                 150
Asp Asn Lys Thr Lys Tyr Leu Gly Arg Pro Tyr Gly Arg Val Ser
               155                 160                 165
Arg Lys Lys Leu Lys Leu Lys Leu Leu Asn Ser Cys Val Glu Asn
               170                 175                 180
Arg Val Lys Phe Tyr Lys Ala Lys Val Trp Lys Val Glu His Glu
               185                 190                 195
```

```
Glu Phe Glu Ser Ser Ile Val Cys Asp Gly Lys Lys Ile Arg
                200                 205                 210
Gly Ser Leu Val Val Asp Ala Ser Gly Phe Ala Ser Asp Phe Ile
                215                 220                 225
Glu Tyr Asp Arg Pro Arg Asn His Gly Tyr Gln Ile Ala His Gly
                230                 235                 240
Val Leu Val Glu Val Asp Asn His Pro Phe Asp Leu Asp Lys Met
                245                 250                 255
Val Leu Met Asp Trp Arg Asp Ser His Leu Gly Asn Glu Pro Tyr
                260                 265                 270
Leu Arg Val Asn Asn Ala Lys Glu Pro Thr Phe Leu Tyr Ala Met
                275                 280                 285
Pro Phe Asp Arg Asp Leu Val Phe Leu Glu Glu Thr Ser Leu Val
                290                 295                 300
Ser Arg Pro Val Leu Ser Tyr Met Glu Val Lys Arg Arg Met Val
                305                 310                 315
Ala Arg Leu Arg His Leu Gly Ile Lys Val Lys Ser Val Ile Glu
                320                 325                 330
Glu Glu Lys Cys Val Ile Pro Met Gly Gly Pro Leu Pro Arg Ile
                335                 340                 345
Pro Gln Asn Val Met Ala Ile Gly Gly Asn Ser Gly Ile Val His
                350                 355                 360
Pro Ser Thr Gly Tyr Met Val Ala Arg Ser Met Ala Leu Ala Pro
                365                 370                 375
Val Leu Ala Glu Ala Ile Val Glu Gly Leu Gly Ser Thr Arg Met
                380                 385                 390
Ile Arg Gly Ser Gln Leu Tyr His Arg Val Trp Asn Gly Leu Trp
                395                 400                 405
Pro Leu Asp Arg Arg Cys Val Arg Glu Cys Tyr Ser Phe Gly Met
                410                 415                 420
Glu Thr Leu Leu Lys Leu Asp Leu Lys Gly Thr Arg Arg Leu Phe
                425                 430                 435
Asp Ala Phe Phe Asp Leu Asp Pro Lys Tyr Trp Gln Gly Phe Leu
                440                 445                 450
Ser Ser Arg Leu Ser Val Lys Glu Leu Gly Leu Leu Ser Leu Cys
                455                 460                 465
Leu Phe Gly His Gly Ser Asn Met Thr Arg Leu Asp Ile Val Thr
                470                 475                 480
Lys Cys Pro Leu Pro Leu Val Arg Leu Ile Gly Asn Leu Ala Ile
                485                 490                 495
Glu Ser Leu
        498

(2) INFORMATION FOR SEQ ID NO:19:

(i) SEQUENCE CHARACTERISTICS:
        (A) LENGTH:498
        (B) TYPE:amino acid
        (C) STRANDEDNESS:double
        (D) TOPOLOGY:linear (xi) SEQUENCE DESCRIPTION:SEQ ID NO:19:

Met Glu Thr Leu Leu Lys Pro Phe Pro Ser Leu Leu Leu Ser Ser
                5                   10                  15

Pro Thr Pro Tyr Arg Ser Ile Val Gln Gln Asn Pro Ser Phe Leu
                20                  25                  30
```

-continued

```
Ser Pro Thr Thr Gln Lys Lys Ser Arg Lys Cys Leu Leu Arg Asn
                 35                  40                  45

Lys Ser Ser Lys Leu Phe Cys Ser Phe Leu Asp Leu Ala Pro Thr
             50                  55                  60

Ser Lys Pro Glu Ser Leu Asn Val Asn Ile Ser Trp Val Asp Pro
             65                  70                  76

Asn Ser Gly Arg Ala Gln Phe Asp Val Ile Ile Gly Ala Gly
             80                  85                  90

Pro Ala Gly Leu Arg Leu Ala Glu Gln Val Ser Lys Tyr Gly Ile
             95                 100                 105

Lys Val Cys Cys Val Asp Pro Ser Pro Leu Ser Met Trp Pro Asn
            110                 115                 120

Asn Tyr Gly Val Trp Val Asp Glu Phe Glu Asn Leu Gly Leu Glu
            125                 130                 135

Asp Cys Leu Asp His Lys Trp Pro Met Thr Cys Val His Ile Asn
            140                 145                 150

Asp Asn Lys Thr Lys Tyr Leu Gly Arg Pro Tyr Gly Arg Val Ser
            155                 160                 165

Arg Lys Lys Leu Lys Leu Lys Leu Leu Asn Ser Cys Val Glu Asn
            170                 175                 180

Arg Val Lys Phe Tyr Lys Ala Lys Val Trp Lys Val Glu His Glu
            185                 190                 195

Glu Phe Glu Ser Ser Ile Val Cys Asp Asp Gly Lys Lys Ile Arg
            200                 205                 210

Gly Ser Leu Val Val Asp Ala Ser Gly Phe Ala Ser Asp Phe Ile
            215                 220                 225

Glu Tyr Asp Lys Pro Arg Asn His Gly Tyr Gln Ile Ala His Gly
            230                 235                 240

Val Leu Val Glu Val Asp Asn His Pro Phe Asp Leu Asp Lys Met
            245                 250                 255

Val Leu Met Asp Trp Arg Asp Ser His Leu Gly Asn Glu Pro Tyr
            260                 265                 270

Leu Arg Val Asn Asn Ala Lys Glu Pro Thr Phe Leu Tyr Ala Met
            275                 280                 285

Pro Phe Asp Arg Asn Leu Val Phe Leu Glu Glu Thr Ser Leu Val
            290                 295                 300

Ser Arg Pro Val Leu Ser Tyr Met Glu Val Lys Arg Arg Met Val
            305                 310                 315

Ala Arg Leu Arg His Leu Gly Ile Lys Val Arg Ser Val Ile Glu
            320                 325                 330

Glu Glu Lys Cys Val Ile Pro Met Gly Gly Pro Leu Pro Arg Ile
            335                 340                 345

Pro Gln Asn Val Met Ala Ile Gly Gly Asn Ser Gly Ile Val His
            350                 355                 360

Pro Ser Thr Gly Tyr Met Val Ala Arg Ser Met Ala Leu Ala Pro
            365                 370                 375

Val Leu Ala Glu Ala Ile Val Glu Gly Leu Gly Ser Thr Arg Met
            380                 385                 390

Ile Arg Gly Ser Gln Leu Tyr His Arg Val Trp Asn Gly Leu Trp
            395                 400                 405

Pro Leu Asp Arg Arg Cys Val Arg Glu Cys Tyr Ser Phe Gly Met
            410                 415                 420
```

```
Glu Thr Leu Leu Lys Leu Asp Leu Lys Gly Thr Arg Arg Leu Phe
            425                 430                 435

Asp Ala Phe Phe Asp Leu Asp Pro Lys Tyr Trp Gln Gly Phe Leu
            440                 445                 450

Ser Ser Arg Leu Ser Val Lys Glu Leu Gly Leu Leu Ser Leu Cys
            455                 460                 465

Leu Phe Gly His Gly Ser Asn Leu Thr Arg Leu Asp Ile Val Thr
            470                 475                 480

Lys Cys Pro Val Pro Leu Val Arg Leu Ile Gly Asn Leu Ala Val
            485                 490                 495

Glu Ser Leu
        498
```

(2) INFORMATION FOR SEQ ID NO:20:

(i) SEQUENCE CHARACTERISTICS:
        (A) LENGTH:56
        (B) TYPE:amino acid
        (C) STRANDEDNESS:single
        (D) TOPOLOGY:linear (xi) SEQUENCE DESCRIPTION:SEQ ID NO:20:

```
Met Glu Ala Leu Leu Lys Pro Phe Pro Ser Leu Leu Ser Ser
            5                   10                  15

Pro Thr Pro Tyr Arg Ser Ile Val Gln Gln Asn Pro Ser Phe Leu
            20                  25                  30

Ser Pro Thr Thr Lys Lys Asn Gln Glu Asn Val Phe Leu Glu Thr
            35                  40                  45

Lys Val Val Asn Phe Phe Val Ala Phe Leu Ile
            50                  55
```

(2) INFORMATION FOR SEQ ID NO:21:

(i) SEQUENCE CHARACTERISTICS:
        (A) LENGTH:26 nucleic acids
        (B) TYPE:nucleic acid
        (C) STRANDEDNESS:double
        (D) TOPOLOGY:linear (xi) SEQUENCE DESCRIPTION:SEQ ID NO:21:

TGACTTCACC CTTCTTTCTT GTCTTC                       26

(2) INFORMATION FOR SEQ ID NO:22:

(i) SEQUENCE CHARACTERISTICS:
        (A) LENGTH:13 nucleic acids
        (B) TYPE:nucleic acid
        (C) STRANDEDNESS:double
        (D) TOPOLOGY:linear (xi) SEQUENCE DESCRIPTION:SEQ ID NO:22:

AGAGTCTGGG TTC                                        13

(2) INFORMATION FOR SEQ ID NO:23:

(i) SEQUENCE CHARACTERISTICS:
        (A) LENGTH:9 nucleic acids
        (B) TYPE:nucleic acid
        (C) STRANDEDNESS:double
        (D) TOPOLOGY:linear (xi) SEQUENCE DESCRIPTION:SEQ ID NO:23:

CTAGTATCG                                               9

```
(2) INFORMATION FOR SEQ ID NO:24:

(i) SEQUENCE CHARACTERISTICS:
        (A) LENGTH:8 nucleic acids
        (B) TYPE:nucleic acid
        (C) STRANDEDNESS:double
        (D) TOPOLOGY:linear (xi) SEQUENCE DESCRIPTION:SEQ ID NO:24:

CTAAATAT                                                                 8

(2) INFORMATION FOR SEQ ID NO:25:

(i) SEQUENCE CHARACTERISTICS:
        (A) LENGTH:10 nucleic acids
        (B) TYPE:nucleic acid
        (C) STRANDEDNESS:double
        (D) TOPOLOGY:linear (xi) SEQUENCE DESCRIPTION:SEQ ID NO:25:

AATTTTCAAA                                                              10
```

TOMATO GENE B POLYNUCLEOTIDES CODING FOR LYCOPENE CYCLASE

FIELD AND BACKGROUND OF THE INVENTION

The present invention relates to a novel polynucleotide sequences isolated from tomato and, more particularly, to a novel lycopene cyclase gene and novel control elements controlling its specific expression in chromogenic tissues of plants, e.g., fruit and flower.

Carotenoids—functions and biosynthesis: Carotenoids comprise one of the largest classes of pigments in nature. In photosynthetic organisms carotenoids serve two major functions—as accessory pigments for light harvesting, and as protective agents against photooxidation processes in the photosynthetic apparatus. Another important role of carotenoids in plants, as well as in some animals, is that of providing distinctive pigmentation. Most of the orange, yellow, or red colors found in the flowers, fruits and other organs of many higher plant species are due to accumulation of carotenoids in the cells.

The biosynthesis of carotenoids has been reviewed extensively (Britton, 1988; Sandmann, 1994a). Carotenoids are produced from the general isoprenoid biosynthetic pathway, which in plants takes place in the chloroplasts of photosynthetic tissues and chromoplasts of fruits and flowers.

The first unique step in carotenoid biosynthesis is the head-to-head condensation of two molecules of geranylgeranyl pyrophosphate (GGPP) to produce phytoene (FIG. 1). All the subsequent steps in the pathway occur in association with membranes. Four desaturation (dehydrogenation) reactions convert phytoene to lycopene via phytofluene, ζ-carotene, and neurosporene, as intermediates. Two cyclization reactions convert lycopene to β-carotene (FIG. 1). Further reactions involve the addition of various oxygen-containing side groups which form the various xanthophyll species (not shown).

It has been established in recent years that four enzymes in plants catalyze the biosynthesis of β-carotene from GGPP: phytoene synthase, phytoene desaturase, ζ-carotene desaturase and lycopene cyclase (reviewed in Sandmann, 1994b). All enzymes in the pathway are nuclear encoded.

Genes for phytoene synthase and phytoene desaturase have been previously cloned from tomato (Ray et al., 1992; Pecker et al., 1992).

The red color of ripe tomatoes is provided by lycopene, a linear carotene which accumulates during fruit ripening as membrane-bound crystals in chromoplasts (Laval-Martin et al., 1975). It is presumed to serve as an attractant of predators that eat the fruit and disperse the seeds. Accumulation of lycopene begins at the "breaker" stage of fruit ripening after the fruit has reached the "mature green" stage. In the "breaker" stage, which is indicated by the commencement of color change from green to orange, chlorophyll is degraded and chloroplasts turn into chromoplasts (Gillaspy et al., 1993; Grierson and Schuch, 1993). Total carotenoid concentration increases between 10 to 15-fold during the transition from "mature green" to "red". This change is due mainly to a 300-fold increase in lycopene (Fraser et al., 1994).

The cDNA which encodes lycopene β-cyclase, CrtL-b, was cloned from tomato (*Lycopersicon esculentum* cv. VF36) and tobacco (*Nicotiana tabacum* cv. Samsun NN, Pecker et al., 1996, U.S. patent application Ser. No. 08/399, 561 and PCT/US96/03044 (WO 96/28014) both are incorporated by reference as if fully set forth herein) and was functionally expressed in *Escherichia coli*. This enzyme converts lycopene to β-carotene by catalyzing the formation of two β-rings, one at each end of the linear carotene. The enzyme interacts with half of the carotenoid molecule and requires a double bond at the C-7,8 (or C-7,8') position. Inhibition experiments in *E. coli* indicated that lycopene cyclase is the target site for the inhibitor 2-(4-methylphenoxy)tri-ethylamine hydrochloride (MPTA, Pecker et al., 1996). The primary structure of lycopene cyclase in higher plants is significantly conserved with the enzyme from cyanobacteria but differs from that of the non-photosynthetic bacteria Erwinia (Pecker et al., 1996). Levels of mRNAs of CrtL-b and Pds, which encodes phytoene desaturase, were measured in leaves, flowers and ripening fruits of tomato. In contrast to genes that encode enzymes of early steps in the carotenoid biosynthesis pathway, whose transcription increases during the "breaker" stage of fruit ripening, the level of CrtL-b mRNA decreases at this stage (Pecker et al., 1996). Hence, the accumulation of lycopene in tomato fruits is apparently due to a down-regulation of the lycopene cyclase gene that occurs at the breaker stage of fruit development. This conclusion supports the hypothesis that transcriptional regulation of gene expression is a predominant mechanism of regulating carotenogenesis.

The search for tissue specific control elements in plants is on going, however, only limited number of tissue specific control elements capable of specifically directing gene expression in chromogenic tissues (fruit, flower) have so far been isolated. These include the promoters of the genes E4 and E8 (Montgomery et al., 1993), which are up-regulated by increase in ethylene concentration during tomato fruit ripening, the tomato gene 2A11 gene (Van Haaren and Houck, 1991) and the polygalacturonase (PG) gene (Nicholass et al., 1995; Montgomery et al., 1993), which are upregulated in tomato fruits during ripening.

There is thus a widely recognized need for, and it would be highly advantageous to have, a novel tissue specific control elements capable of specifically directing gene expression in chromogenic tissues.

The search for structural genes encoding enzymes associated with carotenogenesis is ongoing, and every new gene isolated not only provides insight into carotenogenesis, but also provides a tool to control and modify carotenogenesis for commercial purposes (Hirschberg et al. 1997, Cunningham FX Jr. and Gantt B, 1998).

There is thus a widely recognized need for, and it would be highly advantageous to have, a novel lycopene cyclase capable of altering the composition of carotenoids in carotenoids producing organisms.

SUMMARY OF THE INVENTION

According to one aspect of the present invention there is provided an isolated complementary or genomic DNA segment comprising a nucleotide sequence coding for a polypeptide having an amino acid sequence selected from the group consisting of SEQ ID NOs: 17, 18 and 19 and functional naturally occurring and man-induced variants thereof, with the provision that the polypeptide has a major lycopene cyclase catalytic activity.

According to further features in preferred embodiments of the invention described below, the nucleotide sequence is selected from the group consisting of SEQ ID NOs: 8, 9, 10 and 11 and functional naturally occurring and man-induced variants thereof.

According to still further features in the described preferred embodiments the nucleotide sequence is a cDNA or a genomic DNA isolated form tomato.

According to another aspect of the present invention there is provided a polypeptide comprising an amino acid sequence selected from the group consisting of SEQ ID NOs: 17, 18 and 19 and functional naturally occurring and man-induced variants thereof, the polypeptide having a major lycopene cyclase catalytic activity.

According to another aspect of the present invention there is provided a transduced cell overexpressing a polypeptide including an amino acid sequence selected from the group consisting of SEQ ID NOs: 17, 18 and 19 and functional naturally occurring and man-induced variants thereof, the polypeptide having a major lycopene cyclase catalytic activity, the cell therefore over producing β-carotene on an expense of lycopene.

According to still further features in the described preferred embodiments the transduced cell is selected from the group consisting of a prokaryotic cell and a eukaryotic cell.

According to still further features in the described preferred embodiments the eukaryotic cell is of a higher plant.

According to still further features in the described preferred embodiments the cell forms a part of a transgenic plant.

According to yet another aspect of the present invention there is provided a method of down-regulating production of β-carotene in a cell comprising the step of introducing into the cell at least one anti-sense polynucleotide sequence capable of base pairing with messenger RNA coding for a polypeptide including an amino acid sequence selected from the group consisting of SEQ ID NOs: 17, 18 and 19 and functional naturally occurring and man-induced variants thereof, the polypeptide having a major lycopene cyclase catalytic activity, the cell therefore under producing β-carotene from lycopene.

According to still further features in the described preferred embodiments the at least one anti-sense polynucleotide sequence includes a synthetic oligonucleotide.

According to still further features in the described preferred embodiments the synthetic oligonucleotide includes a man-made modification rendering the synthetic oligonucleotide more stable in cell environment.

According to still further features in the described preferred embodiments the synthetic oligonucleotide is selected from the group consisting of methylphosphonate oligonucleotide, monothiophosphate oligonucleotide, dithiophosphate oligonucleotide, phosphoramidate oligonucleotide, phosphate ester oligonucleotide, bridged phosphorothioate oligonucleotide, bridged phosphoramidate oligonucleotide, bridged methylenephosphonate oligonucleotide, dephospho internucleotide analogs with siloxane bridges, carbonate bridge oligonucleotide, carboxymethyl ester bridge oligonucleotide, carbonate bridge oligonucleotide, carboxymethyl ester bridge oligonucleotide, acetamide bridge oligonucleotide, carbamate bridge oligonucleotide, thioether bridge oligonucleotide, sulfoxy bridge oligonucleotide, sulfono bridge oligonucleotide and a-anomeric bridge oligonucleotide.

According to still further features in the described preferred embodiments the at least one anti-sense polynucleotide sequence is encoded by an expression vector.

According to still further features in the described preferred embodiments the cell is selected from the group consisting of a prokaryotic cell and a eukaryotic cell.

According to still further features in the described preferred embodiments the eukaryotic cell is of a higher plant.

According to still further features in the described preferred embodiments the cell forms a part of a transgenic plant.

According to still another aspect of the present invention there is provided an expression construct for directing an expression of a gene in fruit or flower comprising a regulatory sequence selected from the group consisting of an upstream region of a B allele of tomato and an upstream region of a b allele of tomato.

According to still further features in the described preferred embodiments the expression construct comprising a functional part of nucleotides 1-1210 of SEQ ID NO:14 or nucleotides 1–1600 of SEQ ID NO:15, or functional naturally occurring and man-induced variants thereof.

According to still further features in the described preferred embodiments the expression construct comprising at least one control element having a sequence selected from the group consisting of SEQ ID NOs:21–24, all derived from SEQ ID NO:11, and functional naturally occurring and man-induced variants thereof.

According to still further features in the described preferred embodiments the expression construct is selected from the group consisting of plasmid, cosmid, phage, virus, bacmid and artificial chromosome.

According to still further features in the described preferred embodiments the expression construct is designed to integrate into a genome of a host.

According to yet another aspect of the present invention there is provided a transduced cell or transgenic plant transduced with the above described expression construct.

According to still another aspect of the present invention there is provided a method of isolating a gene encoding a polypeptide having an amino acid sequence homologous to SEQ ID NOs: 17, 18 and 19 and having a major lycopene cyclase catalytic activity from a species, the method comprising the step of screening a complementary or genomic DNA library prepared from isolated RNA or genomic DNA extracted from the species with a probe having a sequence derived from SEQ ID NOs: 8, 9, 10 or 11 and isolating clones reacting with the probe.

The present invention successfully addresses the shortcomings of the presently known configurations by providing novel polynucleotides controlling the expression of genes in fruit and flower in plant and a novel polynucleotide encoding lycopene cyclase.

BRIEF DESCRIPTION OF THE DRAWINGS

The invention herein described, by way of example only, with reference to the accompanying drawings, wherein.

DESCRIPTION OF THE PREFERRED EMBODIMENTS

Figure 1:
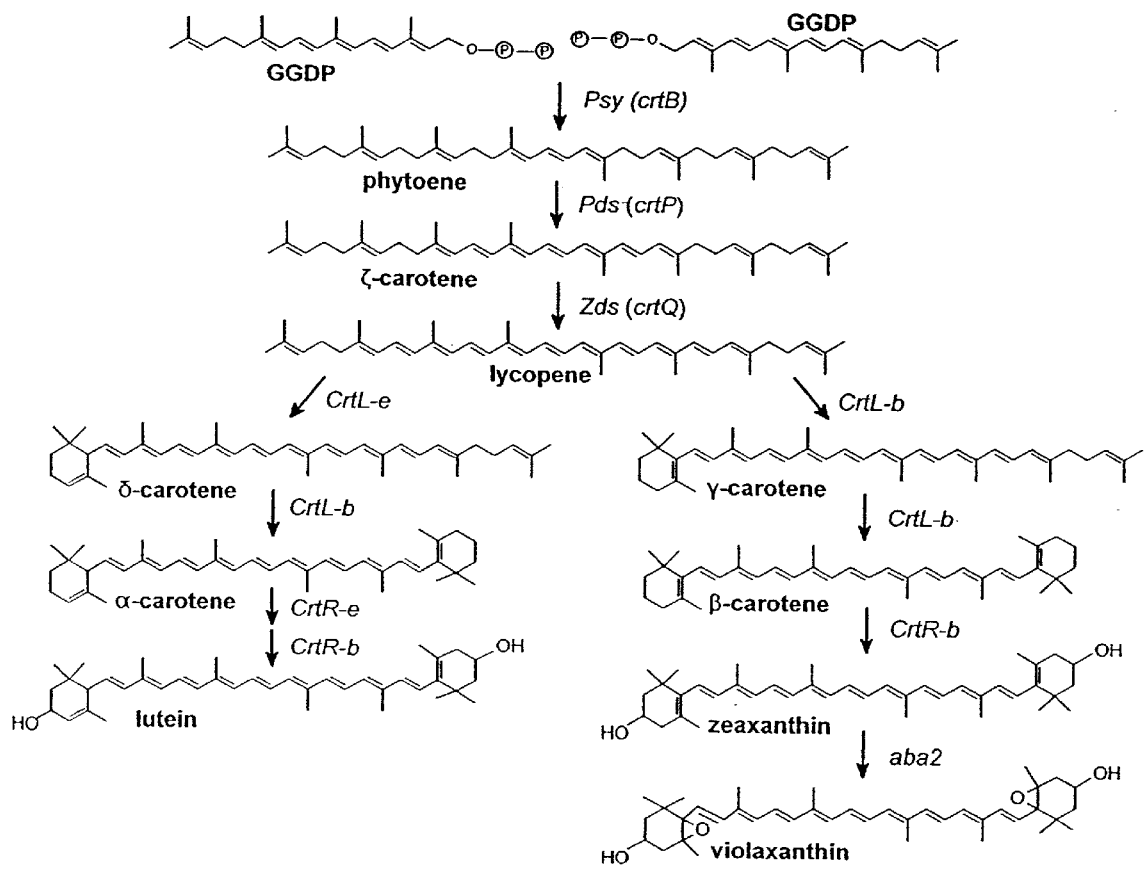
FIG. 1 presents the pathway of carotenoid biosynthesis in plants and algae. Enzymes are indicated by the their gene assignment symbols: aba2, zeaxanthin epoxidase; CrtL-b, Lycopene β-cyclase; CrtL-e, lycopene ε-cyclase; CrtR-b, β-ring hydroxylase; CrtR-e, ε-ring hydroxylase; Pds, phytoene desaturase (crtP in cyanobacteria); Psy, phytoene synthase (crtB in cyanobacteria); Zds, ζ-carotene desaturase (crtQ) in cyanobacteria. GGDP, geranylgeranyl diphosphate.

The present invention is of novel polynucleotide sequences isolated from tomato which can be used to control gene expression in plant chromogenic tissues, especially fruit and flower. The present invention is further of polynucleotide sequences isolated from tomato which encode a lycopene cyclase which can be used to alter carotenogenesis is carotenoids producing organisms.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Fruit of the cultivated tomato (Lycopersicon esculentum) accumulate lycopene, a red carotenoid pigment. A dominant allele of gene B determines accumulation of β-carotene in the fruits of the tomato mutant 'high-beta', at the expense of lycopene, resulting in a unique orange color. Conversion of lycopene to β-carotene in the biosynthesis pathway of carotenoids is catalyzed by the enzyme lycopene β-cyclase. Previously it was shown that CrtL-b, the gene for lycopene β-cyclase, does not map to the locus B in the tomato genetic map. This ruled out the possibility that a mutation in lycopene βcyclase encoded by CrtL-b causes the phenotype in high-beta.

The locus B was mapped to chromosome No. 6. The dominant allele B was found in the tomato introgression line IL 6-2. The DNA of B was identified and cloned by a map-based (positional) cloning method. The nucleotide sequence of this gene was determined and demonstrated a novel type of a lycopene cyclase enzyme. Its primary structure has some similarity to other lycopene cyclases and to the enzyme capsanthin-capsorubin synthase from pepper. In addition, nucleotide sequence was identified, which functions as a strong promoter during fruit development in the B allele of the mutant High-beta.

Thus, according to one aspect of the present invention there is provided an isolated complementary or genomic DNA segment comprising a nucleotide sequence coding for a polypeptide having an amino acid sequence selected from the group consisting of SEQ ID NOs: 17, 18 and 19 and functional naturally occurring and man-induced variants thereof. The polypeptide has a major lycopene cyclase catalytic activity. Polypeptides which share at least 70, 75, 80, 85, 90, 95 or more identical amino acid residues with SEQ ID NOs: 17, 18 or 19 are also within the scope of the present invention.

As used herein in the specification and in the claims section below, the phrase "major lycopene cyclase catalytic activity" refers to catalytic activity mainly directed at the conversion of lycopene to β-carotene by catalyzing the formation of two β-rings, one at each end of the linear carotene, such that if introduced into lycopene-accumulating E. coli cells, such cells accumulate also β-carotene up to a range of at least few percent e.g., 5%, to preferably about 15%, or more, of total carotenoids therein by symmetric formation of two β-ionone rings on the linear lycopene molecules therein.

According to a preferred embodiment of the invention the nucleotide sequence is as set forth in SEQ ID NOs: 8, 9, 10 or 11, or functional naturally occurring or man-induced variants thereof As further shown below these sequences are genomic and complementary DNA sequences which were derived while reducing the present invention to practice from certain tomato cultivars or lines. However, nucleotide sequences which share 70, 75, 80, 85, 90, 95 or more identical nucleotides with SEQ ID NOs: 8, 9, 10 or 11 are also within the scope of the present invention.

According to another aspect of the present invention there is provided a polypeptide comprising an amino acid sequence selected from the group consisting of SEQ ID NOs: 17, 18 and 19 and functional naturally occurring and man-induced variants thereof, the polypeptide having a major lycopene cyclase catalytic activity. Homologous polypeptides as describe above and further detailed hereinunder are also envisaged.

According to another aspect of the present invention there is provided a transduced cell overexpressing a polypeptide including an amino acid sequence selected from the group consisting of SEQ ID NOs: 17, 18 and 19, and functional naturally occurring and man-induced variants thereof, the polypeptide having a major lycopene cyclase catalytic activity, the cell therefore over producing β-carotene on an expense of lycopene.

The cell according to the present invention can be of any type. For example, the cell can be a prokaryotic cell or a eukaryotic cell. Preferably the cell is of a higher plant. The cell preferably forms a part of a transgenic s plant. Methods of transducing cells (and cells in organisms to form transgenic organisms) are well known in the art and do not require further description herein. Protocols are available, for example, in (Sambrook et al., 1989).

As used herein in the specification and in the claims section below, the term "transduced" refers to the result of a process of inserting nucleic acids into cells. The insertion may, for example, be effected by transformation, viral infection, injection, transfection, gene bombardment, electroporation or any other means effective in introducing nucleic acids into cells. Following transduction the nucleic acid is either integrated in all or part, to the cell's genome (DNA), or remains external to the cell's genome, thereby providing stably transduced or transiently transduced cells.

According to yet another aspect of the present invention there is provided a method of down-regulating production of β-carotene in a cell comprising the step of introducing into the cell at least one anti-sense polynucleotide sequence capable of base pairing with messenger RNA coding for a polypeptide including an amino acid sequence selected from the group consisting of SEQ ID NOs: 17, 18 and 19 and functional naturally occurring and man-induced variants thereof, the polypeptide having a major lycopene cyclase catalytic activity, the cell therefore under producing β-carotene from lycopene. Again, the cell can be of any type. For example, the cell can be a prokaryotic cell or a eukaryotic cell. Preferably the cell is of a higher plant. The cell preferably forms a part of a transgenic plant.

As used herein in the specification and in the claims section below, the term "down regulating" means also reducing, lowering, inhibiting, etc., e.g., permanently or transiently reducing.

As used herein in the specification and in the claims section below, the term "production" means also formation or generation.

As used herein in the specification and in the claims section below, the term "introducing" means also providing with or inserting.

The at least one anti-sense polynucleotide sequence according to the present invention can includes one or several synthetic oligonucleotides capable of base pairing with messenger RNA derived from the above-identified nucleotide sequences. The synthetic oligonucleotide preferably includes a man-made modification rendering the synthetic oligonucleotide more stable in cell environment. The modified oligonucleotide can be, for example, a methylphosphonate oligonucleotide, monothiophosphate oligonucleotide, dithiophosphate oligonucleotide, phosphoramidate oligonucleotide, phosphate ester oligonucleotide, bridged phosphorothioate oligonucleotide, bridged phosphoramidate oligonucleotide, bridged methylenephosphonate oligonucleotide, dephospho internucleotide analogs with siloxane bridges, carbonate bridge oligonucleotide, carboxymethyl ester bridge oligonucleotide, carbonate bridge oligonucleotide, carboxymethyl ester bridge oligonucleotide, acetamide bridge oligonucleotide, carbamate bridge oligonucleotide, thioether bridge oligonucleotide, sulfoxy bridge oligonucleotide, sulfono bridge oligonucleotide or an α-anomeric bridge oligonucleotide. For further details the reader is referred to Cook (1991).

Alternatively, the anti-sense polynucleotide sequence is encoded by an anti-sense expression vector. Such vectors are well known in the art and are commercially available from, for example, pBI101, pBI121, pBI221 (commercially available from Colntech.)

Further according to the present invention, there is provided an expression construct for directing an expression of a gene in fruit or flower of a plant. The expression vector according to the present invention includes a regulatory sequence selected from the group consisting of an upstream region of a B allele of tomato and an upstream region of a b allele of tomato. Thus, according to a preferred embodiment of the invention, the expression construct includes a functional part of nucleotides 1–1210 of SEQ ID NO:14 or nucleotides 1–1600 of SEQ ID NO:15, or functional naturally occurring and man-induced variants thereof.

According to a preferred embodiment, the expression construct includes at least one control element having a sequence selected from the group consisting of SEQ ID NOs: 21–24, all derived from SEQ ID NO:11, and functional naturally occurring and man-induced variants thereof.

As further detailed in the Examples section hereinbelow, these sequence elements, which are 26, 13, 9, and 8 bp long and start at (5' end) nucleotides 859, 753, 479 and 306, respectively, of SEQ ID NOs: 11, 15, are located upstream to the initiator methionine codon in the B allele are the main difference between the B and b allele, and are therefore responsible for the differential expression of the B locus in tomato.

The expression construct according to the present invention can be a plasmid, cosmid, phage, virus, bacmid or an artificial chromosome. Each of these constructs has unique sequences rendering the construct most applicable for some as opposed to other applications, as well known in the art. Regardless of its type, according to a preferred embodiment of the present invention the expression construct is designed to integrate into a genome of a host, such that stable transfectants are obtainable. However, the scope of the present invention is not limited to such constructs. In other words, constructs designed for transient transfection are also within the scope of the present invention. In any case, the construct preferably includes at least one positive and/or negative selection gene, and is suitable for transformation, transfection, transgenization and gene knock-in procedures.

According to yet another aspect of the present invention there is provided a transduced cell or a transgenic plant transduced with the above described expression construct. Such a cell or plant is expressing the gene located downstream to the regulatory sequence in a controlled developmental manner, mimicking the expression of the lycopene cyclase gene of the B locus in b or B tomato plants.

According to still another aspect of the present invention there is provided a method of isolating a gene encoding a polypeptide having an amino acid sequence homologous to SEQ ID NOs: 17, 18 and 19 and having a major lycopene cyclase catalytic activity from a species. The method is effected by executing the following method steps, in which a complementary or genomic DNA library prepared from isolated RNA or genomic DNA extracted from the species is screened with a probe having a sequence derived from SEQ ID NOs: 8, 9, 10 or 11 and clones reacting with the probe are isolated. Such clones are good candidates to include segments of genes homologous to SEQ ID NOs: 8, 9, 10 or 11, which genes are good candidates to encode a polypeptide having an amino acid sequence homologous to SEQ ID NOs: 17, 18 and 19. 5' cloning strategies, such as, but not limited to RACE protocols can be employed to isolate full length clones, as well known in the art.

Thus, according to the present invention, the following uses of gene B of tomato are anticipated:

(i) Increasing the content of β-carotene in tissues of transgenic plants over-expressing it. This is an advantageous attribute in fruits and vegetables because it will provide better nutritional value and enhanced color.

(ii) Increasing the accumulation of lycopene in fruits and flowers of transgenic plants by reducing the activity of B using anti-sense inhibition, preferably via anti-sense expression.

(iii) Achieving strong expression of transgenes specifically in fruits and flowers using the promoter sequence of the gene B from High-beta tomato cultivars.

Each of the various and aspects of the present invention as delineated hereinabove and as claimed in the claims section below finds experimental support in the Examples section that follows.

EXAMPLES

Bacteria and plants: *E. coli* strain XL1-Blue was used in all experiments described herein. Tomato (*Lycopersicon esculentum*) CV M82 served as the 'wild-type' strain in the fruit ripening measurements. The introgression lines IL 6-2 and IL 6-3 (Eshed and Zamir, 1994) were used as a source for the B mutation and employed for fine mapping of the B locus.

Figure 2:
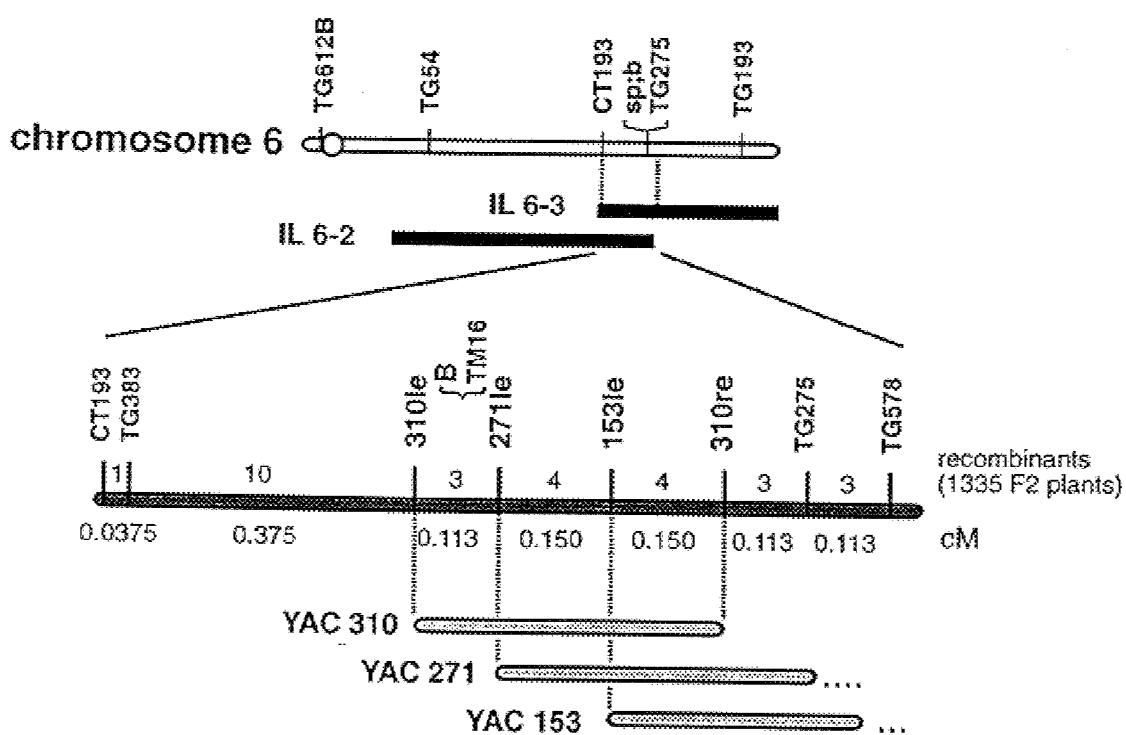
FIG. 2 shows fine genetic mapping and molecular organization of B on chromosome 6 of the tomato linkage map. The linkage map was adopted from Eshed and Zamir (1995). The relevant chromosomal segments from *L. pennellii* that were introgressed to *L. esculentum* lines IL 6-2 and IL 6-3 are represented by black bars. High-resolution genetic map around B is displayed with genetic distances in map units (cM). Positions of the YAC inserts are designated under the map.

Fine mapping and cloning of the B locus: As a source to B mutation, the lines IL-6-2 or IL-6-3 (BB) were used (Eshed and Zamir, 1995). Each line was crossed with the cultivated tomato cv M-82 (bb), and the hybrids were selfed to create an F-2 population that segregated for both he B phenotype and the introgressed DNA segment. 1335 F-2 plants were cored for the RFLP using markers CT193 and TG578 (Pnueli et al., 1998; Tanksley et al., 1992) and for the B phenotype, and recombinant plants were collected. The 32 resulting recombinants were further screened with all the available RFLP probes surrounding B to accurately map the mutated locus (FIG. 2). One RFLP marker, TM16 (Pnueli et al., 1998), was co-segregated with B in less than 0.0375 cM resolution.

The tomato genomic library in YACs was screened with DNA of markers TM16 and TG275. Two overlapping YAC clones, designated 271 and 310, were identified by hybridization. DNA sequences from the ends of the inserts in these YACs were amplified by PCR as previously described (Pnueli et al., 1998) and were used as molecular probes to screen the 32 recombinant plants for Restriction Fragment Length Polymorphism (RFLP). The YAC ends were mapped as shown in FIG. 2. It was established that YAC 310 overlaps the B locus, thus ensured that the 200 kb insert of YAC 310 contains the B gene. In contrast, recombination between the left end of YAC 271 (2711e) and the B phenotype indicated that this YAC clone did not carry the B locus and defined its location in a relatively small region of YAC 310 that did not overlap with YAC 271 (FIG. 2).

The DNA insert of YAC 310 was cut with EcoRI and the resulting fragments were subcloned in the vector λ-gt11. Two phage clones designated B1 and B3, co-segregated with the B locus and mapped to the end of YAC 310. The nucleotide sequence of the insert of B1 was determined. The B 1 fragment was further used to screen a genomic library of wild-type tomato (cv VF36) in the lambda vector EMBL3, and a cosmid library of L. pennellii. A single positive phage clone and a single positive cosmid clone were isolated, respectively.

The B1 fragment was also used to screen 1.5 million plaques of a cDNA library from a tomato fruit and 3 identical clones were isolated. The ca. 1300 bp inserts in these clones contained an open reading frame that was lacking the 5' end, as determined by nucleotide sequence analysis. The full-length cDNAs were then obtained using reverse-transcription polymerase chain reaction (RT-PCR) method with RNA isolated from wild-type (VF-36) and high-beta (IL 6-3)flowers and fruits. For the PCR reaction we used 5' primers based on the genomic sequence taken from the sequence of B1 insert and the 3' primers based on the cloned cDNA. The full coding region of the cDNA of the allele b of wild type tomato (cv. VF-36) and the allele B from L. pennellii were excised in pBluescript KS− vector which were designated pBESC and pBPENN, respectively. DNA sequence comparison between cDNA and genomic sequences revealed no introns interference in the genomic sequence of the b (and B).

DNA blot hybridization was done according to conventional techniques (Sambrook et al., 1989, Eshed and Zamir, 1994) at low stringency in a buffer containing 10×Denharts, 5×SSC, 50 mM phosphate buffer (pH-7), 1% SDS, 50 mg salmon sperm (sheared, autoclaved and boiled before adding to the mixture). Filters were washed with 5×SSC at 65° C.

Genomic DNA of tomato was prepared from 5 grams of leaf as previously described (Eshed and Zamir, 1995).

Amplification by the polymerase chain reaction (PCR) method of the full length cDNA of the b allele was carried out with the following oligonucleotide primers, whose sequence was derived from the genomic sequence of the B1 clone (see below): Forward: 5'-AATGGAAGCTCTTCTCAAGCCT-3' (SEQ ID NO:1), Reverse: 5'-CACATTCAAAGGCTCTCTATCGC-3' (SEQ ID NO:2).

Total RNA was extracted from 1.5 grams of fruit or 0.1 gram of flower or leaf tissues as previously described (Pecker et al., 1996).

Measurement of mRNA levels by the reverse transcription followed by polymerase chain reaction (RT-PCR) technique was carried out as previously described (Pecker et al., 1996) using the following oligonucleotides as primers for the PCR reaction. For amplification of the gene Psy the following primer were employed: Forward1: 5'-TCGAGAACGGACGATG-3' (SEQ ID NO:3), Forward2 (internal): 5'-TGCAGAGAGACAGATG-3' (SEQ ID NO:4) and Reverse: 5'-ATTTCATGCTTTATCTTTGAAG-3' (SEQ ID NO:5).

For amplification of allele B: Forward 5'-GCTGAAGTTGAAATTGTTGA-3' (SEQ ID NO:6) and Reverse 5'-TCTCTTCCTCAATAACACTT-3' (SEQ ID NO:7).

Sequence analysis: DNA sequence analysis was performed by the ABI Prism 377 DNA sequencer (Perkin Elmer) and processed with the ABI sequence analysis software. Nucleotide and amino acid sequence analysis and comparisons were done using the UWGCG software package.

Plasmids: Plasmid pACCRT-EIB for expressing bacterial carotenoid biosynthesis genes in E. coli, was previously described (Cunningham et al., 1993). Plasmid pBESC and pBPENN were constructed by inserting an 1666 bp of cDNA of the tomato B allele (from L. pennellii) or b allele (from L. esculentum), respectively, in the EcoRV site of the plasmid vector pBluescript KS⁻(Stratagene®).

Pigment extraction and analysis: For extraction of pigments from E. coli, aliquots of 2 ml were taken from bacterial suspension cultures. The cells were harvested by centrifugation, washed once with water, resuspended in 2 ml of acetone and incubated at 65° C. for 10 minutes in the dark. The samples were centrifuged again at 13,000 g for 5 minutes and the acetone supernatant containing the pigments was placed in a clean tube. More than 99% of the carotenoids were extracted by this procedure as determined by re-extraction after breaking and grinding the samples. The pigment extract was blown to dryness under a stream of $N_2$ and stored at −20° C. until required for analysis.

Fruit pigments were extracted from 1.0 gram of fresh tissue. The tissue was ground in 2 ml of acetone and incubated at room temperature in the dark for 10 minutes. Then, 2 ml of dichloro-methane were added and the samples were agitated until all pigments were transferred to the supernatant, which was then filtered. To each sample, 4 ml of ether and 0.4 ml of 12% w/v $NaCl/H_2O$ were added and the mixture was shaken gently until all pigment was transferred to the upper (ether) phase. The ether was collected, and the pigment extract was blown to dryness under a stream of $N_2$ and stored at −20° C. until required for analysis.

Carotenoids were separated by reverse phase HPLC using a Spherisorb ODS-2 column (silica 5 mm 3.2 mm×250 mm, Phenomenex®). Samples of 50 µl of acetone-dissolved pigments were injected to a Waters 600 pump. The mobile phase consisted of acetonitrile:$H_2O$ (9:1)—solvent A, and 100% ethyl acetate—solvent B, which were used in a linear gradient between A and B for 30 minutes, at flow of 1 ml per minute. Light absorption peaks were detected in the range of 200–600 nm using a Waters 996 photo diode-array detector. All spectra were recorded in the eluting HPLC solvent, as was the fine absorbance spectral structure. Carotenoids were identified by their characteristic absorption spectra and their typical retention time, which corresponded to standard compounds of lycopene and β-carotene. Peak areas were integrated by the Millennium chromatography software (Waters).

EXPERIMENTAL RESULTS

The only difference between the high-beta mutant and the wild-type tomato is in the fruit color due to accumulation of β-carotene at the expense of lycopene. Thus, it was logical to assume that this mutation occurred in the gene that encodes lycopene-β-cyclase (CrtL-b). However, the CrtL-b cDNA that was previously cloned from tomato (Pecker et al., 1996) was mapped to 2 loci on chromosomes Nos. 4 and 10, but not on chromosome 6, where the B locus was mapped. Even at very low stringency of hybridization conditions we were unable to detect any hybridization of the tomato CrtL-b like sequences on chromosome 6.

Therefore, the only way to clone the gene B, which is responsible for the high-beta phenotype, was to use map-based ("positional") cloning techniques.

Fine mapping of the B locus: As a source to the B mutation, the IL-6-2 or IL-6-3 (BB) (Eshed and Zamir, 1995) tomato lines were employed. Each line was crossed with the cultivated tomato cv. M-82 (bb), and the hybrids were selfed to create an F-2 population that segregated for both the B phenotype and the introgressed DNA segment. 1335 F-2 plants were scored for the RFLP using markers CT-193 and TG-578, (Pnueli et al., 1998; Tanksley et al., 1992) and for the B phenotype, and recombinant plants were collected. The 32 recombinants collected were further screened with all the available RFLP probes surrounding B to accurately map the mutated locus (FIG. 2). One RFLP marker, TM-16 (Pnueli et al., 1998), co-segregated with B in less than 0.0375 cM resolution.

The tomato genomic library in YACs was screened with the DNA marker TM-16 as a molecular probe. Two YAC clones, designated 271 and 310, were identified by hybridization. DNA sequences from the ends of the inserts in these YACs were amplified by PCR as previously described (Pnueli et al., 1998) and were used as molecular probes to screen the 32 recombinant plants for Restriction Fragment Length Polymorphism (RFLP). The YAC ends were mapped as shown in FIG. 2. It was established that YAC 310 overlaps the B locus, thus ensured that the 200 kb insert of YAC 310 contains the B gene. In contrast, recombination between YAC 271 and the B phenotype indicated that this clone did not carry the B locus. Moreover, it established that B was residing in a confined small region of YAC 310 that did not overlap with YAC 271 (FIG. 2).

The DNA insert of YAC 310 was cut with EcoRI and the resulting fragments were subcloned in the vector λ-gt11. Two phage clones designated B 1 and B3, co-segregated with the B locus and mapped to the end of YAC 310. The nucleotide sequence of the insert of B 1 was determined. The B1 fragment was further used to screen a genomic library of wild-type tomato (cv VF36) in the lambda vector EMBL3, and a cosmid library of *L. pennellii*. A single positive phage clone and a single positive cosmid clone were isolated, respectively.

The B1 fragment was also used to screen 1.5 million plaques of cDNA library from a tomato fruit and 3 identical clones were isolated. The ca. 1300 bp inserts in these clones contained an open reading frame that was lacking the 5' end, as determined by nucleotide sequence analysis. The full-length cDNAs were then obtained using reverse-transcription polymerase chain reaction (RT-PCR) method with RNA isolated from wild-type (VF-36) and high-beta (IL 6-3) flowers and fruits. For the PCR reaction we used 5' primers based on the genomic sequence taken from the sequence of B1 insert and the 3' primers based on the cloned cDNA. The full coding region of the cDNA of the allele b of wild type tomato (cv. VF-36) and the allele B from *L. pennellii* were excised in pBluescript KS– vector which were designated pBESC and pBPENN, respectively. DNA sequence comparison between cDNA and genomic sequences revealed no introns interference in the cDNA sequence.

Table 1 below summarizes the sequence data with reference to the sequence listing:

TABLE 1

| Type | allele | Species | SEQ ID NO: |
|---|---|---|---|
| cDNA | b | *L. esculentum* | 8 |
| gDNA | b | *L. esculentum* | 9 |
| cDNA | B | *L. pennellii* | 10 |
| gDNA | B | *L. pennellii* | 11 |
| cDNA | ogC | *L. esculentum* | 12 |
| translated cDNA | b/B | *L. esculentum*/ *L. pennellii* | 13 |
| translated gDNA | b | *L. esculentum* | 14 |
| translated gDNA | B | *L. pennellii* | 15 |
| translated cDNA | ogC | *L. pennellii* | 16 |
| peptide (translated from cDNA) | b | *L. esculentum* | 17 |
| peptide (translated from gDNA) | b | *L. esculentum* | 18 |
| peptide (translated from cDNA) | B | *L. pennellii* | 19 |
| peptide (translated from cDNA) | ogC | *L. esculentum* | 20 | cDNA = complementary DNA; gDNA = genomic DNA; bp = base pairs; aa = amino acid.

Cloning and sequence analysis of old-gold-crimson (ogC) mutation: The old-gold and crimson are two names given to a well-known recessive mutation that was found in the Philippines in 1951 (Butler, 1962 and the SolGenes databases: http:// probe.nal.usda.gov:8300/ cgi-in/webace?db= solgenes & class=Locus & object=og; and: http:// probe.nal.usda.gov:8300/cgi-bin/webace?db=solgenes & class=Image & object=og%2c+old+gold). The ogC locus was mapped to chromosome 6. At least 2000 F-2 progenies of a cross between High-beta (BB) and ogC were screened for B-ogC double mutants and not a single recombinant plant was found. That locates B and ogC less than 0.025 cM apart. The ogC phenotype is characterized by over accumulation of lycopene, both in fruits and flowers, compare to wild type tomatoes and lack of β-carotene in the fruits.

Cloning the B locus from ogC mutant plants was done by PCR method on total genomic DNA extracted from ogC plants using primers that were based on the sequence of the b allele described herein. Sequence analysis of the b-homolog revealed a single base deletion, in the coding sequence of b at position 104 from the initiation codon (compare SEQ ID NOs: 13 and 16). This deletion created a frame-shift mutation that shortened the translatable polypeptide to 56 amino acids. This finding indicates that the ogC is a null mutation of the normal function of the b gene.

Sequences comparison of alleles in the B locus: Nucleotide sequence analysis of the 1666 bp cDNA revealed an open reading frame of 98 codons, potentially coding for a polypeptide of 498 amino acids with a calculated molecular mass of 56.4 kDa. Nucleotide sequence analysis showed 98% identity between b (from VF-36, SEQ ID NO:8) and B (from *L. pennellii*, SEQ ID NO:10). The amino acid sequences of B and b are 97.4% identical (SEQ ID NOs: 17 and 19).

In the 1200 bp sequences upstream to the translated region of B from *L. pennellii* there are four sequence insertions as compared with the equivalent region in b from VF-36. The inserts are 26, 13, 9, and 8 bp long and start at (5' end) nucleotides 859, 753, 479 and 306, respectively, of SEQ ID NOs: 11, 15. They are located upstream to the initiator methionine codon in the B allele are the main difference between the B and b alleles, and are therefore responsible for the differential expression of the B locus in tomato. Their sequences are TGACTTCACCCTTCTTTCT- TGTCTTC (SEQ ID NO:21), AGAGTCTGGGTTC (SEQ ID NO:22), CTAGTATCG (SEQ ID NO:23) and CTAAATAT (SEQ ID NO:24). An additional AATTTTCAAA (SEQ ID NO:25) sequence, which is found in upstream regions of ethylene-activated genes such as E4 and E8 (Montgomery et al., 1993), is shared by the upstream regions of the B and b alleles. All other sequences in the promoter and region are 90–94% conserved in the two allele (compare SEQ ID NOs: 9 and 11).

The polypeptide products of B and b are β-carotene synthases: The use of *E. coli* heterologous system for carotenoid biosynthesis has been proven to be a powerful tool for identifying genes associated with carotenoid biosynthesis. *E. coli* cells of the strain XLI- Blue, carrying the plasmid pACCRT-EIB accumulate lycopene (Cunnungham et al. 1993). Lycopene-accumulating *E. coli* cells were co-transformed with the plasmid pBESC or pBPENN and selected on LB medium containing both ampicillin and chloramphenicol. Carotenoids from cells carrying pACCRT- EIB alone, or pACCRT-EIB and either pBESC or pBPENN were extracted and analyzed by HPLC.

Cells carrying only the pACCRT-EIB plasmid produced lycopene, while cells carrying both pACCRT-EIB and pBPENN accumulate also β-carotene up to 13% of total carotenoids. Similarly, cells carrying both pACCRT-EIB and pBESC produced β-carotene up to 5% of total carotenoids (see Table 2 below). These results indicated that the cDNA-products of both the B and b alleles are capable of converting lycopene to β-carotene by the symmetric formation of two β-ionone rings on the linear lycopene molecule.

TABLE 2

The B gene product converts lycopene to β-carotene. Accumulation of carotenoids in *E. coli* cells expressing alleles B or b from tomato (percent of total carotenoids)

| plasmid | lycopene | β-carotene |
|---|---|---|
| pACCRT-EIB | 100 | |
| pACCRT-EIB + pBESC(b) | 87 | 13 |
| pACCRT-EIB + pBPENN(B) | 95 | 5 |

Sequence comparison between B and other carotene cyclases: The nucleotide sequences of the coding region of b and the coding region of the cDNA of the previously published lycopene β-cyclase from tomato, CrtL-b (Pecker et al, 1996), are 59% identical. The polypeptide products of these genes are only 52% identical. These data explain why CrtL-b could not hybridize with the sequence of B. Moreover, while the similarity in amino acid sequence between B and CRTLB suggests a common mechanism of lycopene cyclization, it clearly demonstrates that B is a novel lycopene β-cyclase enzyme. There is no similarity (less than 45% identities) in the non-translated regions of these two genes.

Surprisingly, the nucleotide sequence of the cDNA of b is 83% identical with the cDNA of a gene from bell pepper (*Capsicum annuum*), which catalyzes the conversion of the ubiquitous 5,6-epoxycarotenoids, antheraxanthin and violaxanthin, into the ketocarotenoids capsanthin and capsorubin, respectively (Bouvier et al., 1994). This enzyme, called also capsanthin-capsorubin synthase (CCS), is synthesized specifically in pepper fruits. There is 85% identity in the deduced amino acid sequences of B and ccS.

Expression of B gene during fruit ripening in wild-type and High-beta: Previously, it has been shown that the steady-state levels of mRNA of the genes for early enzymes in the carotenoid biosynthesis pathway, phytoene synthase and phytoene desaturase, increase during fruit ripening in tomato (Hirschberg et al., 1997). In the case of Pds it was demonstrated that transcriptional up-regulation is responsible for this increase (reviewed in Hirschberg et al., 1997). Recently, we have determined that the mRNA level of CrtL-b, which encodes lycopene β-cyclase, decreases during tomato fruit ripening (Pecker et al. 1996).

Figure 3:
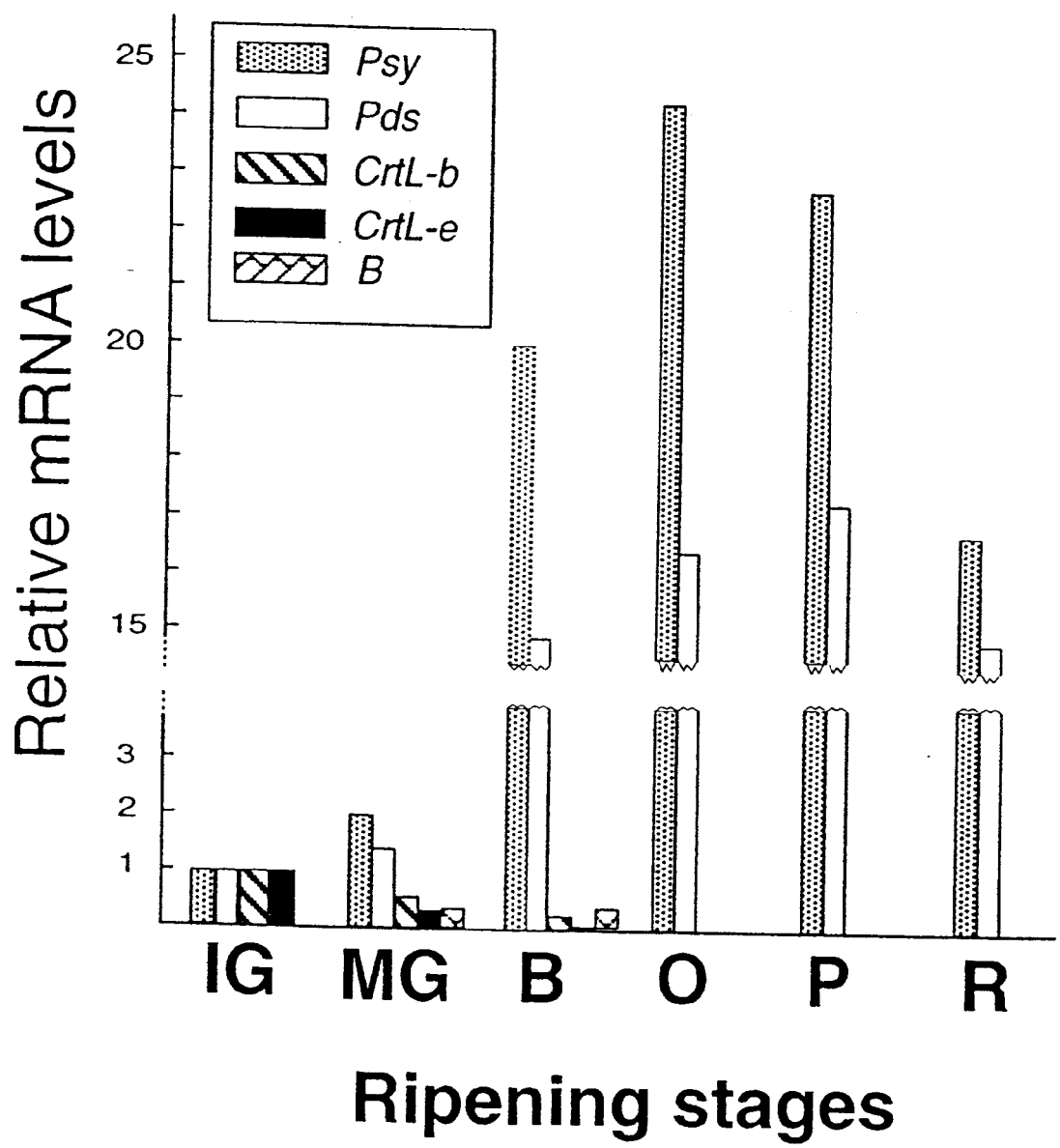
FIG. 3 demonstrates levels of mRNA (relative units) during fruit ripening of wild-type tomato L. esculentum. Data are derived from quantifying the DNA products in the RT-PCR analysis of total RNA extracted at different stages of fruit development. Ripening stages: IG, immature green; MG, mature green, B, breaker, O, Orange; P, pink; R, red.

To determine the regulation of expression of B gene during fruit development in tomato, we have measured by RT-PCR its mRNA level at different stages of fruit development. As can be seen in FIG. 3, mRNA of the b gene is undetected in leaves and during the green stages of fruit ripening of wild-type tomato. However, it is increased at the 'breaker' stage of ripening but then disappears at later stages of ripening. This marked drop of mRNA of B is contrasted by the dramatic increase in mRNA level of Psy at the same stages of fruit ripening.

Figure 4:
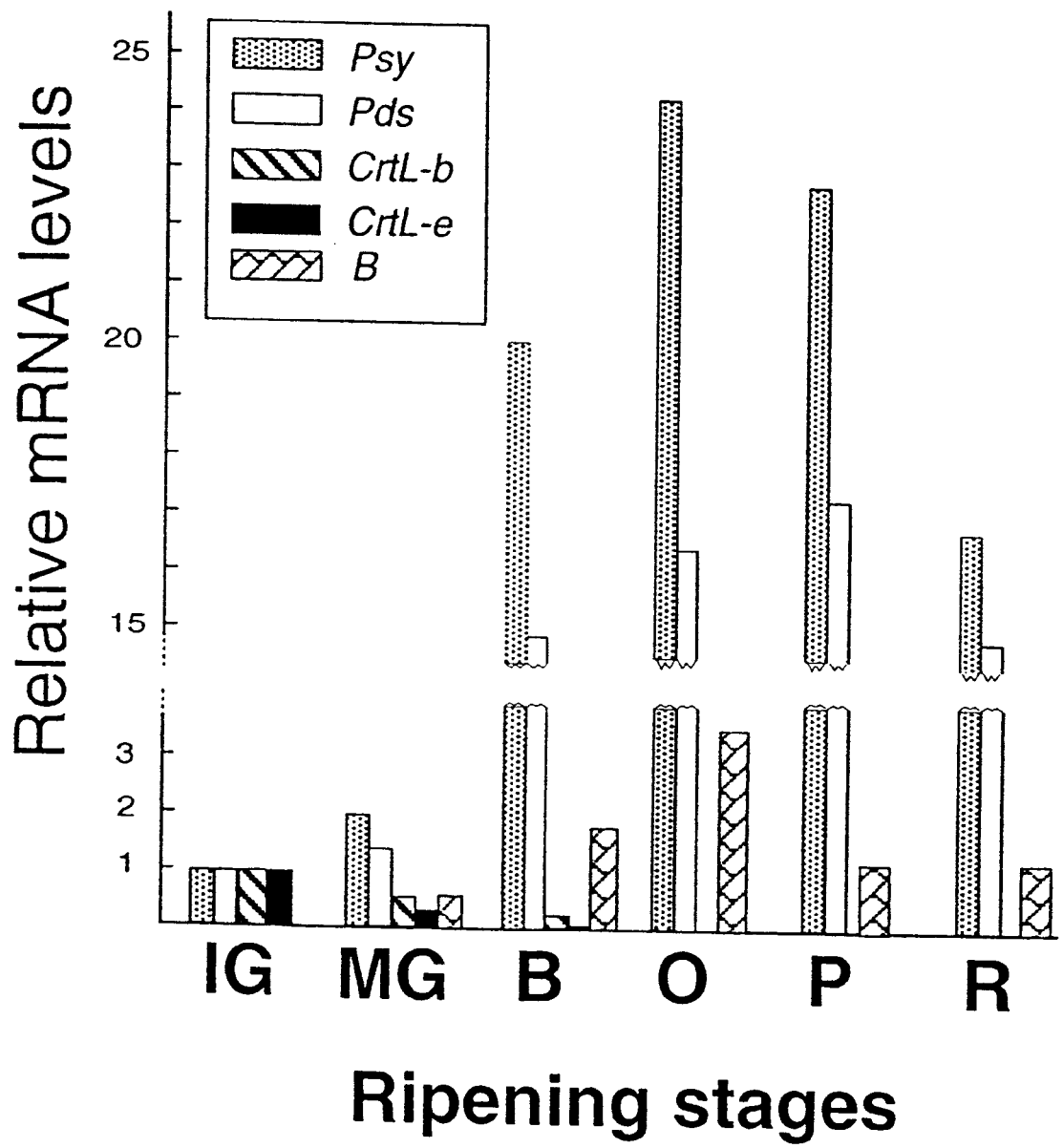
FIG. 4 demonstrates levels of mRNA (relative units) during fruit ripening of the tomato mutant High-beta. Data are derived from quantifying the DNA products in the RT-PCR analysis of total RNA extracted at different stages of fruit development. Ripening stages: G, green; MG, mature green, B, breaker, O, Orange; P, pink; R, red.

In contrast to the wild-type tomato, the mRNA level of B in the fruit of the High-beta mutant (containing the B allele) increases dramatically at the 'breaker' stage and remains high during all the subsequent ripening stages (FIG. 4). These results indicate that the major difference between alleles b and B is in the level of expression at different ripening stages. The results further explain the phenotype of mutant High-beta, carrying the B allele, where a novel type of lycopene cyclase, which is capable of converting lycopene to β-carotene, is highly expressed during fruit ripening.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

REFERENCES CITED IN ALPHABETIC ORDER

1. Bouvier, F., Hugueney, P., d'Harlingue, A., Kuntz, M., and Camara, B. (1994). Xanthophyll biosynthesis in chromoplasts: Isolation and molecular cloning of an enzyme catalyzing the conversion of 5,6-epoxycarotenoid into ketocarotenoid. Plant J. 6:45–54.
2. Britton G (1988) Biosynthesis of carotenoids, Plant Pigments. T W Goodwin, ed, Academic Press), London and New York: pp. 133–180.
3. Butler L, (1962) A new fruit color, Rep. Tomato Genetic Cooperation 12:17–18.
4. Cunningham, F. X., Jr., Chamovitz, D., Misawa, N., Gantt, E., and Hirschberg, J. (1993). Cloning and functional expression in *Escherichia coli* of a cyanobacterial gene for lycopene cyclase, the enzyme that catalyzes the biosynthesis of β-carotene. FEBS Lett. 328:130–138.
5. Cunningham F. X., Jr. and Gantt, E. (1998) Genes and enzymes of carotenoid biosynthesis in plants. Annu. Rev. Plant Physiol. Plant Mol. Biol. 49:557–583.
6. Cook (1991) Medicinal chemistry of antisense oligonucleotides—future opportunities. Anti-Cancer Drug Design 6:585–606.
7. Eshed, Y. and Zamir, D. (1995). An introgression line population of Lycopersicon pennellii in the cultivated tomato enables the identification and fine mapping of yield-associated QTL. Genetics 141:1147–1162.
8. Fraser, P. D., Truesdale, M. R., Bird, C. R., Schuch, W., and Bramley, P. M. (1994). Carotenoid biosynthesis during tomato fruit development. Plant Physiol. 105:405–413.
9. Gillaspy, G., Ben-David, H., and Gruissem, W. (1993). Fruits—a developmental perspective. Plant Cell 5:1439–1451.
10. Grierson, D. and Schuch, W. (1993). Control of ripening. Philos.Trans.R.Soc.Lond.[Biol]. 342:241–250.
11. Hirschberg, J., Cohen, M., Harker, M., Lotan, T., Mann, V., and Pecker, I. (1997). Molecular genetics of the carotenoid biosynthesis pathway in plants and algae. Pure Appl.Chem. 69:2152–2158.
12. Laval-Martin, D., Quennement, J., and Moneger, R. (1975). Pigment evolution in Lycopersicon esculentum during growth and ripening. Biochemistry 14:2357–2362.
13. Mann, V., Pecker, I., and Hirschberg, J. (1994). Cloning and characterization of the gene for phytoene desaturase (Pds) from tomato (*Lycopersicon esculentum*). Plant Mol.Biol. 24:429–434.
14. Montgomery J, Goldman S, Deikman J, Margossian L, Fischer R L, (1993) Identification of an ethylene-responsive region in the promoter of a fruit-ripening gene. Proc. Natl. Acad. Sci. USA 90:5939–5943.
15. Nicholass F J, Smith C J, Schuch W, Bird C R, Grierson D. (1995) High levels of ripening-specific reporter gene expression directed by tomato fruit polygalacturonase gene-flanking regions. Plant Mol Biol 1995 28:423–435.
16. Montgomery J, Pollard V, Deikman J, Fischer R L. (1995) Positive and negative regulatory regions control the spatial distribution of polygalacturonase transcription in tomato fruit pericarp. Plant Cell 5:1049–1062.
17. Pecker, I., Chamovitz, D., Linden, H., Sandmann, G., and Hirschberg, J. (1992). A single polypeptide catalyzing the conversion of phytoene to ζ-carotene is transcriptionally regulated during tomato fruit ripening. Proc.Natl.Acad.Sci.USA 89:4962–4966.
18. Pecker, I., Gabbay, R., Cunningham, F. X., and Hirschberg, J. (1996). Cloning and characterization of the cDNA for lycopene βcyclase from tomato reveals decrease in its expression during fruit ripening. Plant Mol.Biol. 30:807–819.
19. Pnueli, L., Carmel-Goren, L., Hareven, D., Gutfinger, T., Alvarez, J., Ganal, M., Zamir, D., and Lifschitz, E. (1998). The SELF-PRUNING gene of tomato regulates vegetative to reproductive switching of sympodial meristems and is the ortholog of CEN and TFL 1. Development 125:1979–1989.
20. Ray, J. A., Moureau, P., Bird, A. S., Grierson, D., Maunders, M., Truesdale, M., Bramley, P. M., and Schuch, W. (1992). Cloning and characterization of a gene involved in phytoene synthesis from tomato. Plant Mol.Biol. 19:401–404.
21. Sambrook, J., F, Fritch, E., F., and Maniatis, T., 1989. Molecular Cloning: A Laboratory Manual. Cold Spring Harbor Laboratory Press, Cold Spring Harbor. Sandmann, G. (1994a). Phytoene desaturase:
Genes, enzymes and phylogenetic aspects. J.Plant Physiol. 143:444–447.
22. Sandmann, G. (1994b). Carotenoid biosynthesis in microorganisms and plants. Eur.J.Biochem. 223:7–24.
23. Tanksley, S. D., Ganal, M. W., Prince, J. C., de Vicente, M. C., Bonierabale, M. W., Broun, P., Fulton, T. M., Giovanonni, J. J., Grandillo, S., Martin, G. B., Messeguer, R., Miller, J. C., Miller, L., Paterson, A. H., Pineda, O., Roder, M.S., Wing, R. A., Wu, W., and Young, N. D. (1992). High density molecular linkage maps of the tomato and potato genomes. Genetics 132:1141–1160.
24. Van Haaren M J, Houck C M. (1991) Strong negative and positive regulatory elements contribute to the high-level fruit-specific expression of the tomato 2A1 1 gene. Plant Mol. Biol. 17:615–630.
25. Wing, R. A., Zhang, H. B., and Tanksley, S. D. (1994). Map-based cloning in crop plants—tomato as a model system .1. genetic and physical mapping ofjointless. Mol.Gen.Genet. 242:681–688.
26. Zhang, H. B., Martin, G. B., Tanksley, S. D., and Wing, R. A. (1994). Map-based cloning in crop plants: Tomato as a model system .2. Isolation and characterization of a set of overlapping yeast artificial chromosomes encompassing the jointless locus. Mol Gen Genet 244:613–621.

What is claimed is:

1. An isolated polynucleotide encoding a polypeptide having an amino acid sequence at least 95% similar to SEQ ID NO:17, SEQ ID NO:18 or SEQ ID NO:19, wherein said polypeptide has a major lycopene cyclase catalytic activity, said major lycopene cyclase activity comprising production of at least a few percent β-carotene when said polynucleotide is introduced into lycopene-accumulating *E. coli* cells.

2. The isolated polynucleolide of claim 1, having a sequence selected from the group consisting of SEQ ID NO:8, SEQ ID NO:9, SEQ ID NO:10 and SEQ ID NO:11.

3. An isolated *Lycopersicon* polynucleotide comprising a nucleotide sequence having at least 95% identity to SEQ ID NO:8, SEQ ID NO:9, SEQ ID NO:10 or SEQ ID NO:11, wherein said polynucleotide encodes lycopene cyclase.

4. A bacterial or plant cell transformed or transfected with the isolated polynucleotide of claim 1.

5. A transgenic plant comprising the plant cell of claim 4.

* * * * *